United States Patent
Calio et al.

(10) Patent No.: US 7,973,668 B2
(45) Date of Patent: Jul. 5, 2011

(54) AIR SAMPLING SYSTEM HAVING A PLURALITY OF AIR SAMPLING DEVICES WITH THEIR OWN FLOW SWITCHES

(75) Inventors: Rosario Sam Calio, Exton, PA (US); Jeffrey Churchvara, Downingtown, PA (US)

(73) Assignee: Veltek Associates, Inc., Malvern, PA (US)

( * ) Notice: Subject to any disclaimer, the term of this patent is extended or adjusted under 35 U.S.C. 154(b) by 0 days.

(21) Appl. No.: 12/723,095

(22) Filed: Mar. 12, 2010

(65) Prior Publication Data

US 2010/0283620 A1 Nov. 11, 2010

Related U.S. Application Data

(63) Continuation-in-part of application No. 12/402,738, filed on Mar. 12, 2009, which is a continuation-in-part of application No. 12/068,483, filed on Feb. 7, 2008.

(60) Provisional application No. 61/305,669, filed on Feb. 18, 2010.

(51) Int. Cl.
*G08B 21/00* (2006.01)
(52) U.S. Cl. ............... 340/606; 454/187; 73/863.03
(58) Field of Classification Search .......... 340/603, 340/606, 609; 73/863, 863.01–863.03; 454/187; 700/215–217
See application file for complete search history.

(56) References Cited

U.S. PATENT DOCUMENTS

| | | | |
|---|---|---|---|
| 4,091,674 A | 5/1978 | Amey | |
| 4,604,111 A | 8/1986 | Natale | |
| 4,663,293 A | 5/1987 | Hempel et al. | |
| 4,813,984 A | 3/1989 | Griffis | |
| 5,421,214 A | 6/1995 | Burgdorfer | |
| 5,553,496 A | 9/1996 | Nishiyama et al. | |
| 5,645,480 A | 7/1997 | Spengler | |
| 5,831,182 A | 11/1998 | Swenson | |
| 5,838,008 A | 11/1998 | Esler et al. | |
| 6,125,710 A | 10/2000 | Sharp | |
| 6,167,107 A | 12/2000 | Bates | |
| 6,167,766 B1 | 1/2001 | Dunn et al. | |
| 6,216,548 B1 | 4/2001 | Park et al. | |
| 6,230,080 B1 | 5/2001 | Lee et al. | |
| 6,295,864 B1 | 10/2001 | You et al. | |

(Continued)

OTHER PUBLICATIONS

Veltek Associates, Inc., One Touch Command™ SMA™ Microbial Air Sampling Systems Brochure, Revised Dec. 2002, 4 pgs., Malvern, Pennsylvania.

*Primary Examiner* — Jeffery Hofsass
(74) *Attorney, Agent, or Firm* — Blank Rome LLP

(57) ABSTRACT

A system for sampling air in a controlled environment that includes two or more air sampling devices at different locations within the controlled environment. A controller is provided at a location outside of the controlled environment and in separate air flow communication with each air sampling devices via separate first vacuum tubes. A flow switch for each of the air sampling devices is provided at a location between a corresponding air sampling device and the vacuum source, each of the flow switches being configured to separately measure and control the rate of air flow through a corresponding first vacuum tube. An alarm is automatically activated at a location inside the controlled environment by one or more of the flow switches when the rate of air flow measured at one or more of the flow switches deviates from a desired value by a predetermined amount.

20 Claims, 19 Drawing Sheets

U.S. PATENT DOCUMENTS

| | | |
|---|---|---|
| 6,425,297 B1 | 7/2002 | Sharp |
| 6,514,721 B2 | 2/2003 | Spurrell |
| 6,532,835 B1 | 3/2003 | Saaski et al. |
| 6,692,953 B1 | 2/2004 | Sugita et al. |
| 6,867,682 B2 * | 3/2005 | Reinhardt et al. ............ 340/3.5 |
| 7,667,839 B2 | 2/2010 | Bates |

* cited by examiner

AIR SAMPLING SYSTEM HAVING A PLURALITY OF AIR SAMPLING DEVICES WITH THEIR OWN FLOW SWITCHES

RELATED APPLICATIONS

This application claims the benefit of U.S. Provisional Application Ser. No. 61/305,669, filed Feb. 18, 2010, and is a continuation-in-part of U.S. application Ser. No. 12/402,738, filed Mar. 12, 2009, which is a continuation-in-part of U.S. application Ser. No. 12/068,483, filed Feb. 7, 2008, the disclosures of which are hereby incorporated in their entirety by reference.

BACKGROUND OF THE INVENTION

1. Field of the Invention

The present invention relates to devices and methods for collecting air samples in indoor environments. In particular, the present invention relates to devices and methods for collecting, processing, and analyzing air samples in clean rooms and electronically and automatically controlling and calibrating the sampling equipment from a single, central location.

2. Description of the Related Art

Clean rooms found in manufacturing, research, and other facilities are typically classified into two broad categories based on the static air pressure inside the rooms relative to atmospheric pressure and/or based on the air pressure in spaces adjacent the clean rooms. A positive air pressure room is maintained at an absolute air pressure greater than atmospheric pressure, greater than the air pressure in spaces adjacent the clean room, or both. The positive air pressure in such rooms is provided by pumping filtered and/or conditioned air into the rooms and controlling the flow of air out of the rooms. The adjacent spaces, which may be manufacturing facilities or offices, are typically maintained at or close to atmospheric pressure by heating, ventilation, and air conditioning (HVAC) systems, or by providing an opening to the environment that allows the adjacent spaces to equilibrate with atmospheric pressure. Thus, air flowing from the positive pressure clean room will flow toward the lower pressure in adjacent rooms or to the atmosphere.

When a positive air pressure clean room is breached, air flowing to adjacent spaces or the atmosphere is generally not a problem as long as airborne contaminants present in the clean room do not pose a potential adverse health effect to people in the adjacent spaces. Typically, the air inside clean rooms in which electronics, aerospace hardware, optical systems, military equipment, and defense-related research are manufactured or conducted may not contain airborne gases, vapors, and particulate matter at concentrations that present a safety or health concern to human health or the environment. However, that is not always the case, as other operations within those industries may generate contaminants that are above acceptable levels and, therefore, must be prevented from escaping the clean room without treatment.

A negative air pressure room is maintained at an absolute air pressure that is either less than atmospheric pressure, less than the air pressure in spaces adjacent the clean room, or both. The negative pressure is maintained by pumping air out of the room at a rate faster than that at which filtered and/or conditioned air is pumped into the room. Negative pressure rooms are often used when there is a concern that contaminants in the air in the room may pose a potential health threat to human health in adjacent spaces or the environment.

Notwithstanding the human health and environmental implications, certain types of manufacturing and research operations must be conducted within a positive air pressure clean room to satisfy regulatory requirements and industry-adopted good manufacturing and laboratory quality control standards. For example, state and federal regulations, including those promulgated by the National Institute for Occupational Safety and Health (NIOSH), may necessitate the use of positive or negative pressure clean rooms.

In particular, the U.S. Food & Drug Administration (FDA) requires that pharmaceutical production be done within the confines of clean rooms that provide for the validation and certification that manufactured batches of pharmaceutical products are being produced in a sanitary environment.

Positive and negative air pressure clean rooms have been used for many years. U.S. Pat. No. 4,604,111, for example, discloses a negative pressure apparatus and method for protecting the environment and populations from airborne asbestos and other particulate contamination inside a building, which includes an enclosure having a blower to pull air into a filtration unit inside the enclosure and dispel the filtered air to the atmosphere. U.S. Pat. No. 5,645,480 discloses the general features of a clean room.

Various FDA regulations and standards also specify requirements for air sampling and/or air monitoring equipment to be used inside clean rooms to verify or validate the cleanliness of the facility during certain drug manufacturing activities. The regulations also provide for electronic data recording, accuracy, precision, and record-keeping relating to monitoring the air quality within clean rooms. Similar requirements are imposed on other industries, such as the biotechnology industry.

U.S. Pat. No. 6,514,721 describes an air sampling device and method for collecting airborne pathogens and psychrometric data from a room or from remote air samples where the sample volume is electronically controlled by closely monitoring fan speed. That patent illustrates a device that draws room air into a sampling device using a pump, which causes pathogen-containing particulates in the air to impact a growth/inhibitor media (a solid, liquid, gel, or mixture thereof) stored in a dish that is positioned within the sampling device. The patent states that previous sampling devices could not achieve a constant volumetric air flow of better than ±30% relative to a nominal or set-point flow rate, which caused a large variability in calculated concentrations of pathogens.

As U.S. Pat. No. 6,514,721 patent suggests, one of the keys to successfully monitoring the air quality within a clean room is to ensure that the air flow rate through the air sampling/monitoring devices is very accurately determined during the time when a volume of air is collected. That fact is also appreciated in U.S. Pat. No. 4,091,674, which discloses an electronically timed, positive displacement air sampling pump for use with a wide variety of air sample collecting devices and in a wide range of environmental conditions. The disclosed invention is said to provide accurate average flow rate, independently metered total volume, operating time register, and audible "rate fault" alarm. In that patent, accuracy is achieved by using a timing circuit coupled with a mechanical bellows.

U.S. Pat. No. 6,216,548 illustrates a control system flow chart for an air sampling device for use in a controlled environment. In particular, the patent discloses a controller logic that involves turning on a pump, checking pressure, monitoring sampling time, drawing air into the sampler, shutting off the pump, and checking for leaks in the lines. The patent also teaches using a purge system for purging the lines and associated air particulate sampler using a purge gas such as nitrogen gas. In that patent, air sampling only occurs at one location (e.g., a processing chamber for semiconductor devices).

None of the prior art devices and air sampling methods described above is suitable for monitoring the level of contaminants in the air of a modern clean room. For example, a volumetric air flow accuracy not better than ±30% relative to a nominal or set-point flow rate, mechanical bellows, and single-location sampling are not sufficient where issues of sample volume accuracy and precision are important at multiple locations in a clean room. Accordingly, there is a need for an air sampling system and method that has a flow rate accuracy better than ±30%, a digital flow switch, and simultaneous multi-location sampling.

In addition, none of the prior art devices provide the degree of control, monitoring, reporting, modularity, and remote operation required in the modern clean room. For example, none of the prior art devices and air sampling methods described above utilizes multiple air sampling devices with inline digital flow switches at each air sampling device to separately and simultaneously measure the air flow realized at each individual air sampling device. Nor do any of the prior art devices and air sampling methods described above provide the ability to simultaneously monitor and control a variable number of air sampling devices placed at different locations in a clean room from a single, central location that is remote from the air sampling devices. Accordingly, there is also a need for an air sampling system and method that allows the user to separately and simultaneously measure, monitor, and control varying numbers of air sampling devices from a single, central location.

SUMMARY AND OBJECTS OF THE INVENTION

An air sampling/monitoring system and method in accordance with the present invention overcomes at least the shortcomings of the prior art discussed above by providing two or more air sampling devices at different locations within the controlled environment. A controller is provided at a location outside of the controlled environment and in separate air flow communication with each of the two or more air sampling devices via separate first vacuum tubes, the controller having a manifold configured to separately control a rate of air flow from the two or more air sampling devices to the controller via each of the separate first vacuum tubes and to selectively direct the air flow from each of the separate first vacuum tubes to one or more second vacuum tubes. A vacuum source is provided at a location outside the controlled environment and in air flow communication with the controller via the one or more second vacuum tubes, the vacuum source providing suction and being controlled by the controller to generate the air flow through each of the first vacuum tubes. And, a flow switch for each of the two or more air sampling devices is provided at a location between a corresponding air sampling device and the vacuum source, each of the flow switches being configured to separately measure and control the rate of air flow through a corresponding first vacuum tube. An alarm is automatically activated at a location inside the controlled environment by one or more of the flow switches when the rate of air flow measured at one or more of the flow switches deviates from a desired value by a predetermined amount.

With those and other objects, advantages, and features of the invention that may become hereinafter apparent, the nature of the invention may be more clearly understood by reference to the following detailed description of the invention, the appended claims and to the several drawings attached herein.

BRIEF DESCRIPTION OF THE DRAWINGS

Many aspects of the present invention can be better understood with reference to the following drawings, which are part of the specification and represent preferred embodiments of the present invention. The components in the drawings are not necessarily to scale, emphasis instead being placed upon illustrating the principles of the present invention. And, in the drawings, like reference numerals designate corresponding parts throughout the several views.

DETAILED DESCRIPTION OF THE PREFERRED EMBODIMENTS

Figure 1:
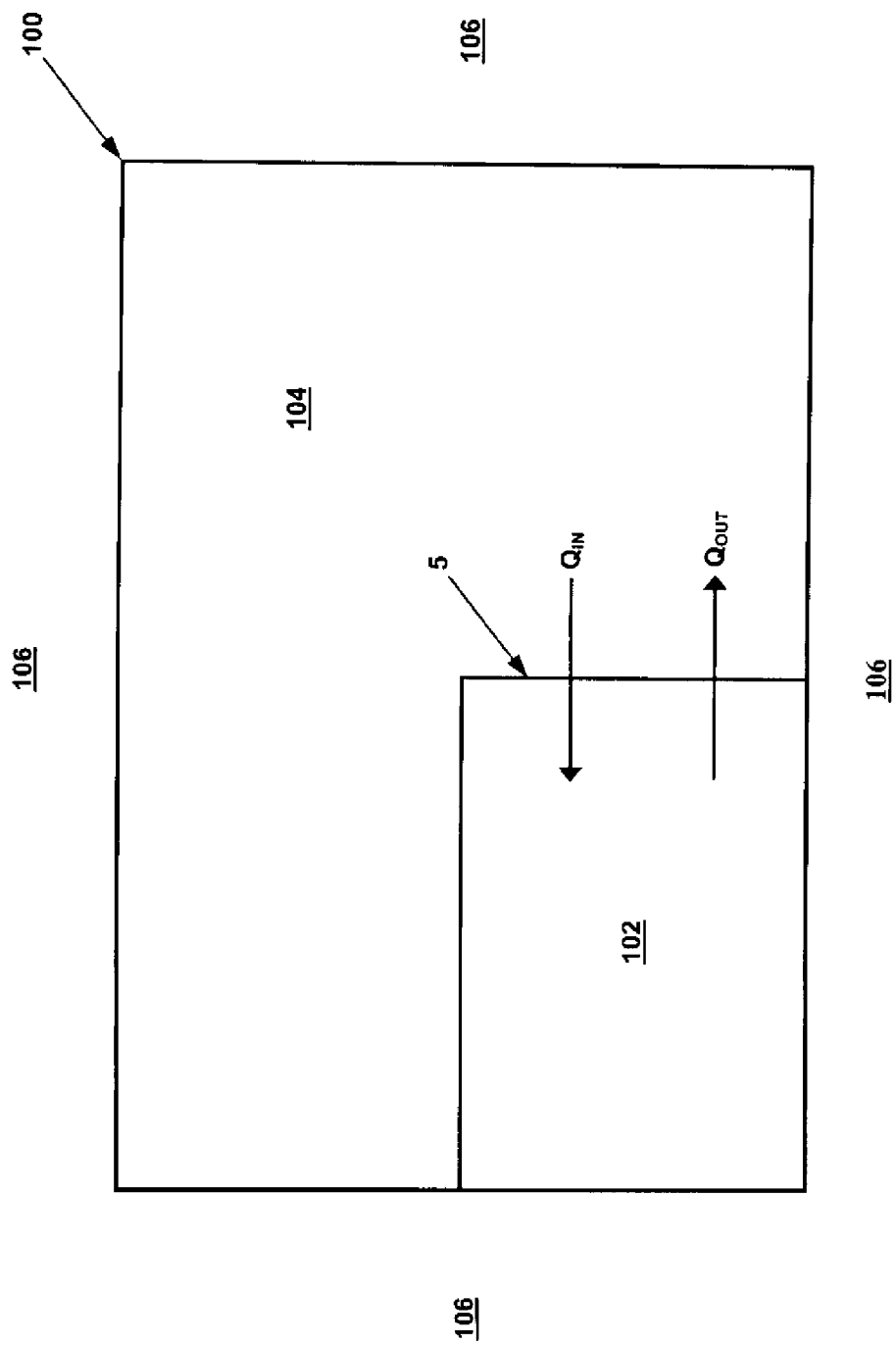
FIG. 1 is a schematic diagram of an exemplary facility having a clean room therein according one aspect of the present invention.

Several preferred embodiments of the invention are described for illustrative purposes, it being understood that the invention may be embodied in other forms not specifically shown in the drawings.

Turning first to FIG. 1, shown therein is a schematic of an exemplary facility 100 having one or more clean rooms 102 therein. The clean room 102 is surrounded by an adjacent space 104 and the outdoor atmosphere 106. The adjacent space 104 may be one or more rooms within the same facility 100 in which the clean room 102 is located and that adjoin the clean room 102, such as, for example, a separate manufacturing room, another clean room, a finish and fill room, a research laboratory, offices, etc. The clean room 102 and adjacent space 104 are separated by a divider, such as a wall 5.

The clean room 102 in the exemplary facility 100 is capable of being maintained at an air pressure $P_1$ that is less than or greater than the air pressure $P_2$ of the adjacent space 104 and atmospheric air pressure $P_{ATM}$ of the outdoor atmosphere 106. That is accomplished by an HVAC system (not shown) that causes conditioned and filtered air to be pumped into the clean room 102 at a controlled flow rate $Q_{IN}$ as depicted in FIG. 1. Air inside the clean room 102 that is pumped out of or otherwise flows out of the clean room 102 is represented by $Q_{OUT}$. When the difference between $Q_{IN}$ and $Q_{OUT}$ (i.e., $Q_{IN}-Q_{OUT}$) is greater than zero, a positive pressure will be maintained in the clean room 102. And, when the difference between $Q_{IN}$ and $Q_{OUT}$ is less than zero, a negative pressure will be maintained in the clean room 102.

Figure 2:
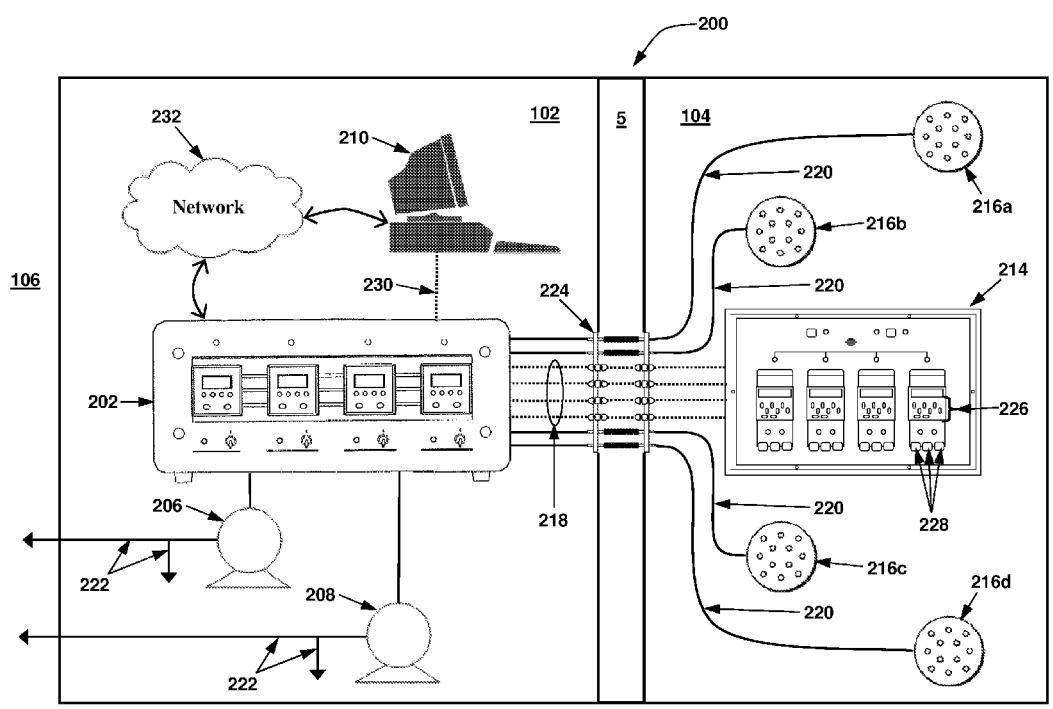
FIG. 2 is a schematic diagram of an air sampling/monitoring system for use in the clean room of FIG. 1 according to a non-limiting embodiment of the present invention.

Turning now to FIG. 2, shown therein is a schematic diagram of an air sampling/monitoring system 200, according to one embodiment of the present invention, for use in sampling or monitoring the air in the clean room 102. The air sampling/monitoring system 200 includes a controller 202 (front view shown), a vacuum pump 208, an optional purge pump 206, and an optional computing device 210, all of which may be co-located together in the adjacent space 104, adjacent to or remote from (i.e., not directly adjacent to) the clean room 102.

Remotely connected to the controller 202 are a stand-alone wall-mountable or benchtop touchpanel 214 and four air sampling devices 216a, 216b, 216c, and 216d, but that number is not limited by the air sampling/monitoring system 200 to any particular quantity of air sampling devices 216. That is, the system 200 is linearly scalable to substantially any number n of air sampling devices 216a, 216b, 216c, . . . , and 216n, wherein n is preferable 10 (i.e., 216a, 216b, 216c, . . . , and 216j). A typical air sampling device suitable for use with the present invention is the SMA ATRIUM brand air sampling device made by Veltek Associates, Inc., Malvern, Pa. The air sampling devices 216a, 216b, 216c, . . . , and 216n according to the present invention may be any known air sampling device for collecting a volume of air. The terms "collecting," "sampling," "monitoring," and the like are not used to refer just to whole air sampling devices, but also to refer to devices that process the flow of fluid in order to separate certain gases, vapors, and particulate matter in the fluid for subsequent analysis and quantification. The terms "air" and "fluid" are used interchangeably to refer to gases, vapors, and particulates. Thus, "air sampler" does not mean that only air is being collected and/or monitored.

In addition, although FIG. 2 shows a single touchpanel 214 connected to four air sampling devices 216a, 216b, 216c, and 216d, it is also contemplated that there may be other arrangements of touchpanels and air sampling devices. For example, there may be a one-to-one ratio of individual or discrete touchpanels 214 and air sampling devices 216a, 216b, 216c, . . . , and 216n, or a single touchpanel 214 may be connected to three air sampling devices 216a, 216b, and 216c while a separate touchpanel 214 is connected to a fourth air sampling device 216d.

The touchpanel 214 is in electrical communication with the controller 202 via signal wires 218, or using wireless means such as an internal receiver/transmitter (not shown) provided with the controller 202 and an internal receiver/transmitter (not shown) provided with the touchpanel 214. In the figures, certain signal wires (e.g., signal wires 218) are represented by dotted lines to illustrate that those signal wires are not necessary when wireless receiver/transmitters are employed by the devices placed in electrical communication by those signal wires. Wireless communications can be implemented over a data communications network (not shown) using a Frequency Hopping Spread Spectrum (FHSS) integrated radio with digital input/outputs and signals. The data communications network may be any proprietary or public network, including a packet-switched network, such as the Internet. The receiver/transmitters used to transmit data over such a network may be configured to use the same high frequency, which is unique to the overall air sampling/monitoring system 200. The frequency is selected so as to reduce the likelihood of interference.

The four illustrated sampling devices 216a, 216b, 216c, and 216d are connected to a vacuum pump 208 (described in more detail below) by way of the controller 202 using one or more air tubes 220, which may be ¼-inch (inside diameter) vacuum tubing on the clean room 102 side of the air sampling/monitoring system 200 and ⅜-inch (inside diameter) vacuum tubing on the adjacent space 104 side of the air sampling/monitoring system 200. Other sized tubing may also be used. The one or more air tubes 220 are connected to a wall-mounted quick disconnect outlet 224 located at the wall 5 in between the clean room 102 and the adjacent space 104. Within the controller 202 is a manifold (not shown) that ties all of the individual air tubes 220 together and connects them to the vacuum side of the vacuum pump 208. Individual solenoids (not shown) associated with the air tubes 220 are used to turn on the air flow to each air sampling device 216 so that any combination of sampling devices 216a, 216b, 216c, and/or 216d can be employed simultaneously to perform sampling cycles at various locations throughout the clean room 102.

The touchpanel 214 and air sampling devices 216 are co-located together in the clean room 102, or in a portion of the clean room 102. The touchpanel 214 serves as a remote command center for operating the controller 202, which is located outside of the clean room 102. The touchpanel 214 includes various indicators 226 for identifying which air sampling devices 216a, 216b, 216c, and/or 216d are being used for air sampling, and includes various input mechanisms, such as switches 228, for signaling to the controller 202 which air sampling devices 216a, 216b, 216c, and/or 216d to operate. The touchpanel 214 therefore eliminates the need for the user to leave the clean room 102 to operate the controller 202 (i.e. to start and stop flow at the air sampling devices 216a, 216b, 216c, and/or 216d).

The vacuum pump 208 is a demand pump that operates upon receiving a signal from the controller 202 to operate at the beginning of an air sampling cycle. It is powered by a standard alternating current (AC) power source (not shown) provided by the facility 100 in which the air sampling/monitoring system 200 is installed, by power from the controller 202, or both. The vacuum pump 208 is connected to the controller 202 using ¾-inch (inside diameter) vacuum tubing. Other size tubing may also be used. The vacuum pump 208, according to one embodiment of the present invention, is a 1.5 HP motor vacuum pump. The discharge from the vacuum pump 208 is directed to the outside atmosphere 106 or within the adjacent space 104 as needed, as shown by discharge tubes 222.

The optional purge pump 206 may be connected to the controller 202 using ¼-inch (inside diameter) vacuum tubing. Other size tubing may also be used. The discharge from the purge pump 206 is also directed to the outside atmosphere 106 or within the adjacent space 104 as needed. The discharge will most likely be processed through an abatement system (not shown) to collect or scrub purge gases and contaminants collected during the purge cycle (described below).

The computing device 210 may be used as a data recorder. The computing device 210 may be a dedicated computing device connected directly to the controller by signal wire 230 or wirelessly over a data communications network 232. The computing device 210 may include an internal receiver/transmitter (not shown) to facilitate that wireless communication. The data communications network 232 may be any proprietary or public network, including a packet-switched network, such as the Internet, a local area network, a wireless network, or a combination of networks. The communications network 232 may use a FHSS integrated radio with digital input/outputs and signals, with the receiver/transmitters of the controller 202 and the computing device 210 being on the same high frequency that is unique to the overall air sampling/monitoring system 200.

Data recorded by the computing device 210 may include, among other data, the time a sample was taken, the date a sample was taken, the length of time over which a sample was taken, and the location a sample was taken. In addition to data logging, the computing device 210 may also be used as a portal for remotely monitoring and controlling the sampling/monitoring system 200. Accordingly, each of the functions described below for each of the components of the sampling/monitoring system 200 can be performed remotely via the computing device 210.

To facilitate the remote monitoring and control of the sampling/monitoring system 200, the computing device 210 may include any suitable computing processor or processing platform that is capable of performing the functions and operations in accordance with the invention. The computing platform is preferably, for instance, a Field Programmable Gate Array (FPGA) or an Application-Specific Integrated Circuit (ASIC), either in a stand alone system. All or parts of the of the sampling/monitoring system 200 and the processes required to remotely monitor and control the of the sampling/monitoring system 200 can be stored on or read from a memory or computer-readable media.

The processor and memory used to monitor and control the sampling/monitoring system 200 can be implemented using any suitable computing device 210 (e.g., a Personal Computer (PC), such as a laptop or tablet PC, a Secure Mobile Environment Portable Electronic Device (SME PED), and a Personal Digital Assistant (PDA)). The computing device 210 includes a display for the user to monitor the status of the various components of the sampling/monitoring system 200 and includes a user interface, such as a keyboard, key pad, or touch screen, for the user to input instructions for controlling the sampling/monitoring system 200. Accordingly, an image representing the component being monitored or controlled can be shown on the display (i.e., an image representing the front of the controller 202 (e.g., FIG. 4), the touchpanel 214 (e.g., FIG. 7), the inline flow control modules 904 (e.g., FIG. 10), and/or the digital flow enclosure 1602 (e.g., FIG. 17)), or any other suitable image, to allow the user to see exactly what is occurring within the sampling/monitoring system 200 in real time and to make real-time decisions regarding which control instructions to initiate. That functionality adds a large degree of flexibility to the sampling/monitoring system 200, enabling a clean room 102 to be monitored and controlled remotely from substantially any location. Moreover, the computing device 210 can be connected to any number of sampling/monitoring systems 200 at any number of locations, thereby providing a mechanism for monitoring and controlling multiple clean rooms 102 from a single, central location. And, the same functionality may be provided via a secure website from which a user can remotely monitor and control any number of sampling/monitoring systems 200 over the Internet from virtually any location, adding yet another degree flexibility and accessibility to the present invention.

Figure 3:
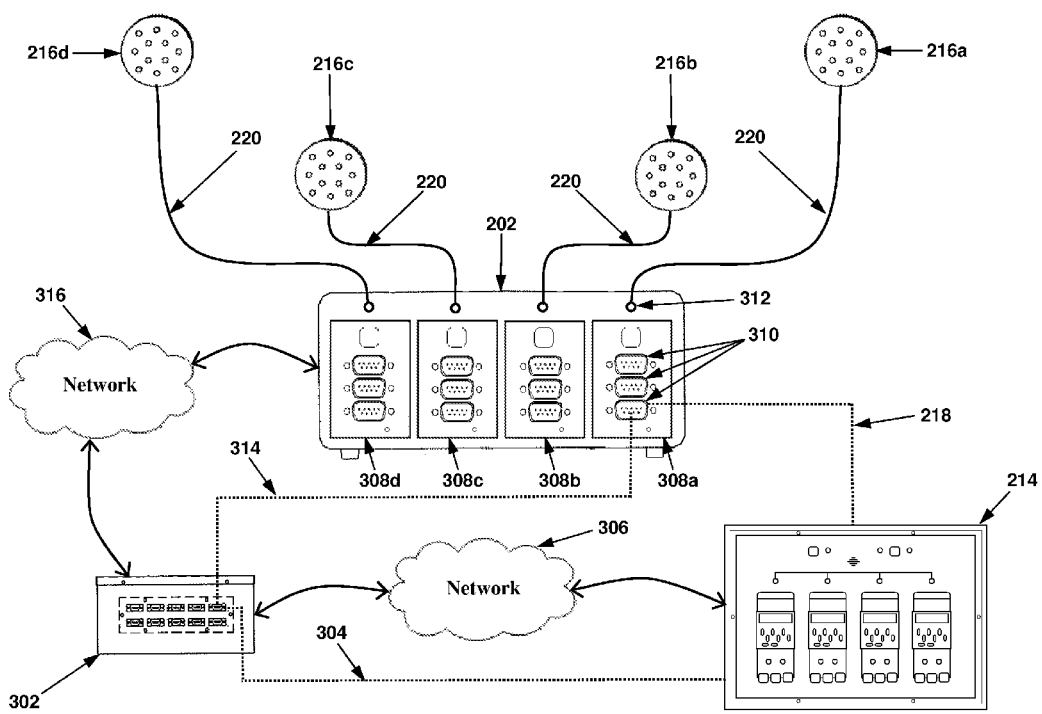
FIG. 3 is a schematic diagram of a controller connected to a base station and a touchpanel according to a non-limiting embodiment of the present invention.

Turning now to FIG. 3, shown therein is a schematic diagram of a controller 202 (rear view shown) of the present invention connected to a touchpanel base station 302 and a touchpanel 214. The controller 202 includes four modular ports 308a, 308b, 308c, and 308d for connecting the controller 202 to the four separate air sampling devices 216a, 216b, 216c, and 216d, respectively, and one touchpanel 214. The controller 202, however, may have any number n of modular ports 308a, 308b, 308c, . . . , and 308n and corresponding touchpanels 214 and sampling devices 216a, 216b, 216c, . . . , and 216n. The simplest configuration would be a single controller 202 having a single port 308a in one room, connected to one or more air sampling devices 216a and a single touchpanel 214 in another room. An additional port 308b can then be added to the controller 202 to connect with an additional one or more air sampling devices 216b, and the touchpanel 214 can be updated to have an interface that controls the second air sampling device 216b, or a second touchpanel 214 may be used. The touchpanel 214 and air sampling device 216b of the port 308b can be in the same room as the touchpanel 214 and the air sampling device 216a for the port 308a, but in a different area of that room, or can be in an entirely different room. The ports 308a, 308b, 308c, . . . , and 308n are further modular because they include their own dedicated power, hardware, and software, including fittings and connectors necessary for operation. In other words, the modularity makes the system easily configurable by adding or removing ports 308a, 308b, 308c, . . . , and/or 308n to connect with individual touchpanels 214 and their associated one or more air sampling devices 216a, 216b, 216c, . . . , and 216n, respectively.

Although FIG. 3 shows the touchpanel 214 connected to a single port 308a, it can be connected to each of the ports 308a, 308b, 308c, and 308d and, indirectly, to each of the air sampling devices 216a, 216b, 216c, and 216d, respectively. The controller 202 passes signals between the touchpanel 214 and the sampling device 216a, 216b, 216c, or 216d connected to a particular port 308a, 308b, 308c, or 308d. Thus, the control signals sent from the touchpanel 214 or the port 308a are sent to the air sampling device 216a also connected to that same port 308a, but not to the air sampling devices 216b, 216c, and 216d connected to the other ports 308b, 308c, and 308d.

Because the controller 202 is modular, it may have any number n of ports 308, depending upon the needs of the clean room 102 (or clean rooms 102), as specified, for example, in the individual facility air sampling protocol, standard operating procedures, quality assurance/quality control plans, regulations, etc. For example, the controller 202 may be used to control 1, 2, 3, . . . n individual air sampling devices 216a, 216b, 216c, . . . , and 216n deployed within one or more clean rooms 102, in which case it will have a corresponding number n of ports. Preferably, one or more of the individual air sampling devices 216a, 216b, 216c, . . . , and/or 216n and one touchpanel 214 are connected to each one of the individual ports 308a, 308b, 308c, . . . , and 308n.

Each of the individual ports 308a, 308b, 308c, . . . , and 308n includes at least one connector 310 for connecting the individual ports 308a, 308b, 308c, . . . , and 308n to data loggers, such as the computing device 210, or to other devices. Preferably, at least two multi-pin connectors 310 are used. Pairs of multi-pin connectors 310 are electrically connected in parallel. A suitable multi-pin connector 310 would include, but is not limited to, a 9-pin connector. Each of the individual ports 308a, 308b, 308c, . . . , and 308n also includes at least one air tube interface 312 for connecting the individual ports 308a, 308b, 308c, . . . , and 308n to the individual air sampling devices 216a, 216b, 216c, . . . , and 216n.

The touchpanel base station 302 can be used for wired or wireless communication between the controller 202 and the touchpanel 214. The touchpanel base station 302 may be needed as an intermediary device to relay signals between the controller 202 and the touchpanel 214 when those two components are located a large enough distance apart that a single, continuous signal wire 218 becomes too long to be a convenient or effective means of signal transport. The base station may also be needed as an intermediary device to relay signals between the controller 202 and the touchpanel 214 when those two components are located a large enough distance apart that a direct wireless connection cannot be made. And, the touchpanel base station 302 may be needed to facilitate wireless communication between the controller 202 and the touchpanel 214 when either the controller 202 or the touchpanel 214 is provided without an internal receiver/transmitter to facilitate wireless communications therebetween. The touchpanel base station 302 may be provided with a receiver/transmitter (not shown) to facilitate such wireless communications.

The touchpanel base station 302 may be co-located with the controller 202, or otherwise outside the clean room 102, or it may be co-located with the touchpanel 214 inside the clean room 102. The touchpanel base station 302 acts primarily as a data communications relay between the touchpanel 214 and the controller 202 and it may be operatively connected to the either the touchpanel 214 or the controller 202 via a data communications network 306 and 316. The data communications network 306 and 316 may be any proprietary or public network, including a packet-switched network, such as the Internet, a local area network, a wireless network, or a combination of networks. The communications network 306 and 316 may use a FHSS integrated radio with digital input/outputs and signals. The receiver/transmitter of the touchpanel base station 302 is on the same high frequency that is unique to the overall air sampling/monitoring system 200.

The touchpanel base station 302 interface operates as a two-way (point-to-point) monitoring and control device with expandable input/output options. For example, when the touchpanel 214 is provided without an internal receiver/transmitter for wireless communications, it can be connected to the base station by signal wire 304 and the receiver/transmitter of the touchpanel base station 302 will facilitate wireless communications with the controller 202 via wireless network 316. And, when the controller 202 is provided without an internal receiver/transmitter for wireless communications, it can be connected to the base station by signal wire 314 and the receiver/transmitter of the touchpanel base station 302 will facilitate wireless communications with the touchpanel 214 via wireless network 316. Both of those configurations eliminate the need for the touchpanel 214 to be directly connected to the controller 202 by signal wire 218. The receiver/transmitters used to facilitate such wireless communications are a dedicated pair that only communicate with each other.

When the controller 202 and the touchpanel 214 communicate, the touchpanel 214 connects to input/output circuit boards (not shown) at the controller 202 that signal to the touchpanel 214 whether the individual ports 308a, 308b, 308c, . . . , and 308n are powered up, are in an air sampling mode, and/or experience an air flow error during an air sampling cycle. In that way, the touchpanel 214 can detect the state of activity of each of the individual ports 308a, 308b, 308c, . . . , and 308n at the controller 202, thereby allowing a user to determine where in the facility 100 sampling is being conducted (i.e., which air sampling devices 216a, 216b, 216c, . . . , and/or 216n are presently being operated) and at which air sampling devices 16a, 216b, 216c, . . . , and/or 216n any errors occur. The touchpanel 214 can also be used to remotely start and stop sampling at various air sampling devices 216a, 216b, 216c, . . . , and 216n within the facility 100, thereby eliminating the need for the user to access the controller 202 directly to perform that function.

Figure 4:
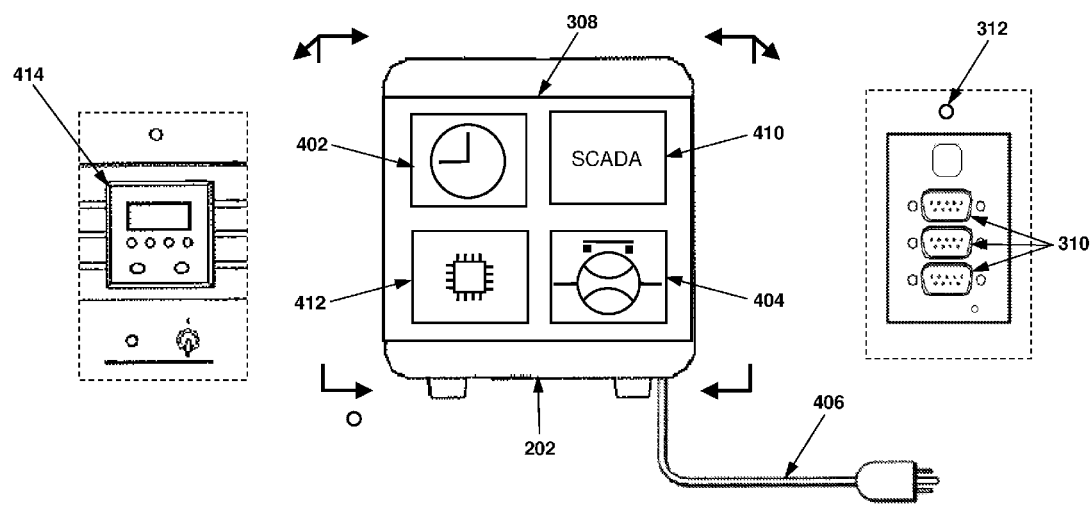
FIG. 4 is a schematic diagram of a port of the controller shown in FIG. 3 according to a non-limiting embodiment of the present invention.

Turning now to FIG. 4, shown therein is a schematic diagram of an exemplary port 308 of the controller 202 according to one embodiment of the present invention. The port 308 has its own dedicated timer 402, air flow switch 404, direct current (DC) power supply, air tube interface 312, two multi-pin connectors 310, facility System Control and Data Acquisition (SCADA) interface 410, 1 CFM circuit board 412, and digital air flow display 414. The port 308 is modular and independent of other ports associated with the controller 202, as previously described. Thus, in the event the port 308 fails, the remaining ports associated with the controller 202 can continue to function within calibrated tolerances. The modular design also removes the possibility of a single point system failure.

The port 308 has its own DC power supply that it converts from the controller's 202 AC power supply 406 and it is, therefore, not dependent on a centralized power source to operate. Ground loop or DC voltage shifts are eliminated by using optical coupling circuits (not shown), thus providing stable and robust performance. Those circuits isolate the SCADA DC voltage and ground distribution system from the controller's 202 DC voltage and ground distribution system (not shown). When interconnected with another system within the facility 100 (e.g., a central monitoring system), the sampling/monitoring system 200 will not depend on a common DC ground bus connection with that facility system, which enables those two systems to be interconnected with long cables without requiring an extraordinary DC ground interconnection. Thus, when the facility system sends and receives current signals that are referenced to that system's DC voltage and ground distribution system, the problems associated with interconnecting two systems with different power requirements are safely and effectively eliminated. For example, those features allow the sampling/monitoring system 200 to be connected directly to a computing device 210, such a PC, provided within the facility 100.

The dedicated timer 402 is used to monitor the air sampling cycle duration. The timer 402 may be located at the controller 202 outside the clean room 102, or at the touchpanel 214 inside the clean room 102 and connected to the controller 202 via signal wire 218. The status of the timer 402 for the port 308 is observable at the controller 202 via its digital air flow display 414 and/or at the touchpanel 214 via its indicators 226. Each timer 402 may run independently or simultaneously with other ports 308. The timer 402 may be calibrated to a known standard to obtain very accurate readings. The timer 402 starts the air sampling cycle and issues commands through its input/output to open solenoids (not shown) and start the vacuum pump 208. The timer 402 signals to the air flow switch 404 that a sampling cycle has been initiated so the computing device 412 can determine if the proper air flow is present. The timer 402 also provides +12 volts DC power to other components of each port 308 and/or touchpanel 214.

The controller 202 has an internal interface 410 that can connect to a customer's SCADA interface, and/or a processor 412 or programmable logic controller (PLC) that can interface with a central monitoring system associated with the facility 100 (e.g., a system that monitors conditions in multiple rooms throughout the facility). The controller 202 includes an isolator interface (not shown) that will not create any voltage shifts or ground loops when connected to other systems in the facility 100 or other components of the sampling/monitoring system 200. Voltage shifts and ground loops can cause information problems for the facility 100 and/or the controller 202. The purge mode of the controller 202 is not interfered with or affected by the wireless controls or isolation interface input/outputs of the system 200.

The air flow switch 404 includes a digital air flow display 414 that may be programmed to display air flow rates in liters per minute (LPM), cubic feet per minute (CFM), or other units. The nominal or set-point volumetric flow rate through each of the one or more air sampling devices 216a, 216b, 216c, and 216d is 1 CFM (or 30 LPM). That is accomplished by the 1 CFM circuit board 412 and the air flow switch 404. The air flow switch 404 generates an error signal if the air flowing through the port 308 during an air sampling cycle, T, does not meet a pre-programmed or set-point 1 CFM air flow value or satisfy pre-determined tolerances. The signal allows the user to be alerted to a problem with a particular air sample. Because the air flow switch 404 is a digital switch, it may be easily calibrated against a standard flow switch (such as a National Institute of Standards and Technology-certified switch), and it is insulated from negative effects caused by pressure variations in the air flow tubing and/or the location of the air flow switch 404. Use of a digital air flow switch also eliminates internal piping variations from component to component or system to system, and it has an integrated flow adjustment pinch valve, which reduces piping. Use of a digital flow switch substantially eliminates those problems.

The air flow switch 404 is mechanically and electrically connected to the air tube interface 312, which receives the air tube 220 to provide fluid communication between the air flow switch 404 of the port 308 and a remote air sampling device 216, as shown, for example, in FIG. 2. While a digital air flow switch 404 is preferred, a float type meter (rotameter) could also be used, if pressure variations are taken into account. Rotameters are less desirable because, among other things, it may be necessary to provide a calibration conversion device and computed transfer function when using a rotameter. And, the rotameter must be positioned at a suitable level and angle to permit accurate manual readings.

The air flow switch 404 is located between the one or more air sampling devices 216a, 216b, 216c, . . . , and 216n and the 1 CFM circuit board 412 and is designed to maintain a steady-state flow rate through the one or more air sampling devices 216a, 216b, 216c, . . . , and 216n and associated air tubing 220, with a detectable air flow rate deviation tolerance of ±3 percent from the nominal set-point flow rate (typically, the concern is when the flow rate decreases 3% from the nominal set-point flow rate). That air flow rate accuracy, which provides a margin of error of about 2 percent for a system calibrated for ±5 percent, for example, is achieved through a combination of routine and non-routine calibration checks using a standard flow switch, as discussed above, and software and hardware that constantly monitors flow rate in real-time or near real-time. The air flow switch 404 is programmed to send an error signal to the 1 CFM circuit board 412 when the air flow is below the programmed set-point or low-flow value. That is, the flow switch 404 informs the 1 CFM circuit board 412 that the air flow is below the 3-percent minimum level programmed into the system. The 1 CFM circuit board 412 checks to ensure the air flow rate error is valid. If the 1 CFM circuit board 412 confirms the validity of the air flow, it sends a signal to the individual port 308a, 308b, 308c, . . . , or 308n that is performing the air sampling.

Figure 16:
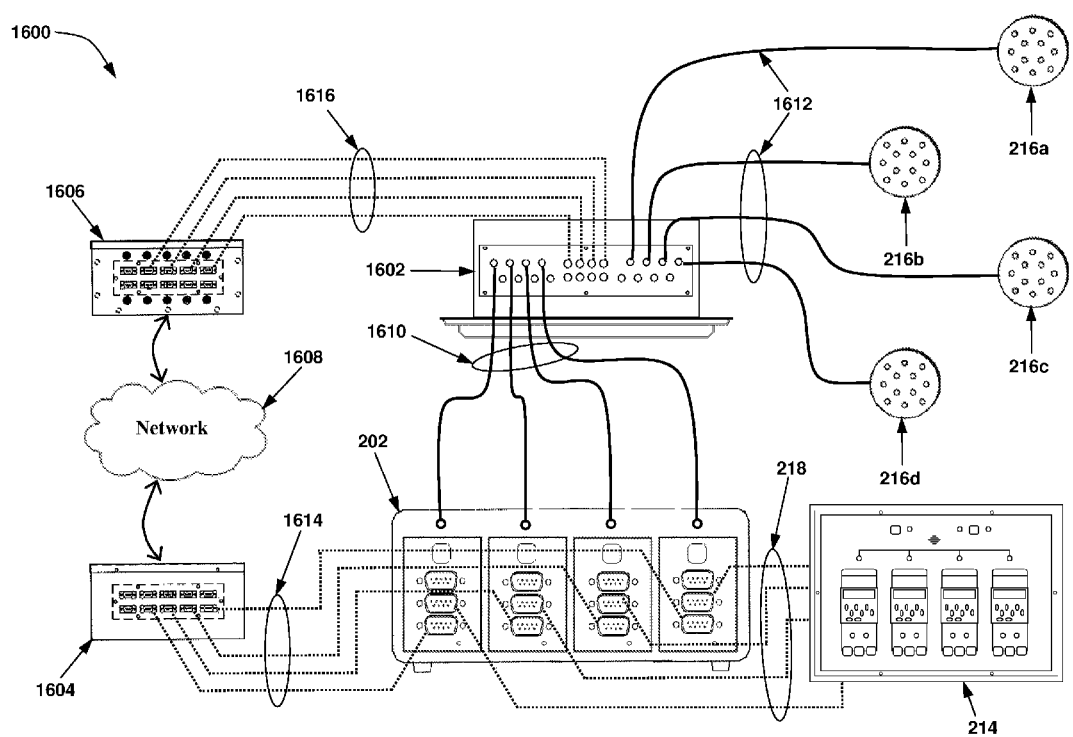
FIG. 16 is a schematic diagram of an air sampling/monitoring system for use in the clean room of FIG. 1 according to yet another non-limiting embodiment of the present invention.

The flow switch 404 has low and high set-points, which are programmable. When the air flow is too far above or below the set-point values, the flow switch 404 sends a digital "on" signal to the 1 CFM circuit board 412 that the air flow is in error. The 1 CFM circuit board 412 is active during an air sampling cycle, and a signal from the flow switch 404 will cause the 1 CFM circuit board 412 to send or broadcast a flow error to the controller 202, touchpanel 214, isolator controller 504 (FIG. 5), and digital flow enclosure 1602 (FIG. 16).

The SCADA interface 410 allows the port 308 to connect to a facility SCADA, which allows the sampling/monitoring system 200 to be integrated into other data collection and monitoring systems at the facility 100, such as the computing device 210. In addition to data logging, when the computing device 210 is integrated into the sampling/monitoring system 200 in that manner, the images representing the different components of the sampling/monitoring system 200 (e.g., the image representing the front of the controller 202 (e.g., FIG. 4), the touchpanel 214 (e.g., FIG. 7), the inline flow control modules 904 (e.g., FIG. 10), and the digital flow enclosure 1602 (e.g., FIG. 17)) can be populated in real time with the corresponding data from the sampling/monitoring system 200 to create a real-time "virtual" reproduction of that component on the computing device. The isolation interface prevents the sampling/monitoring system 200 from compromising the controller or the SCADA system performance by eliminating ground loops and voltage shifts when connecting to third-party equipment, as previously described.

The port 308 may be directly connected to, or interconnected to, the computing device 210 via its multi-pin connections 310, or wirelessly, in addition to being connected to the touchpanel 214. As discussed above, the computing device 210 has software and hardware to implement the functions of the port 308. The controller 202 may also have a central processor (not shown) so that the computing device 210 can communicate with that processor to control the overall operation of the controller 202 and its ports 308a, 308b, 308c, . . . , and 308n.

Figure 5:
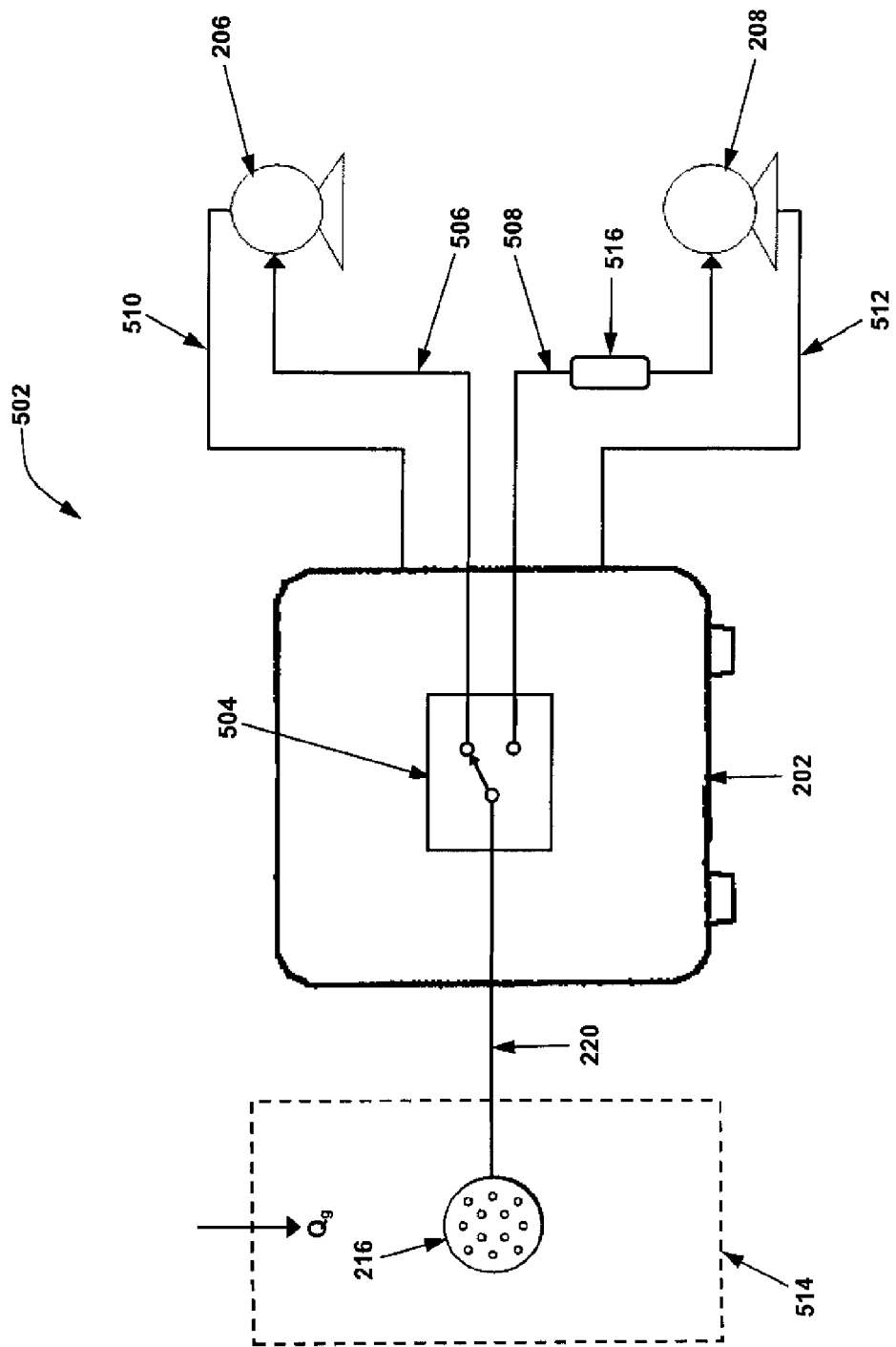
FIG. 5 is a schematic diagram of a purge system for purging the air sampling devices according to a non-limiting embodiment of the present invention.

Turning now to FIG. 5, shown therein is a purge system 502 for purging the air sampling devices 216a, 216b, 216c, . . . , and 216n and associated air tubes 220 to ensure there are no residual contaminants in those portions of the sampling/monitoring system 200. An isolator controller 504 provided in the controller 202 controls the operation of the vacuum pump 208 and purge pump 206 in accordance with an air sampling cycle and a purge cycle. In the air sampling cycle, the isolator controller 504, which can be a three-way solenoid, causes the vacuum pump 208 to stop by sending a signal to the vacuum pump 208 via signal wire 512. At the same time, the isolator controller 504 controls the purge pump 206 to engage by sending a signal to the purge pump 206 via signal wire 510. When those signals are sent, air is not pulled through the air sampling devices 216a, 216b, 216c, . . . , and 216n and air tube 508 by the vacuum pump 208, but is instead pulled through the air sampling devices 216a, 216b, 216c, . . . , and 216n and air tube 506 by the purge pump 206. Thus, during the air sampling cycle, air flow is steered to the vacuum pump 208 and the purge path is closed. The opposite is done during the purge cycle, whereby air flow is steered to the purge pump 206 and the air sampling path is closed.

Although the isolator controller 504 preferably is associated with up to 10 individual ports 308a, 308b, 308c, . . . , and 308j and corresponding air sampling devices 216a, 216b, 216c, . . . , and 216j, FIG. 5 shows only one air sampling device 216. During any air sampling cycle, the controller 202 is prevented from initiating a purge cycle. However, once the air sampling cycles for each of the air sampling devices 216 are complete, the controller 202 is set in the purge mode. The isolator controller 504 ports each have a dedicated solenoid (not shown) that will direct the air collected during the purge cycle to a discharge tube 222, as best seen in FIG. 2.

Figure 6:
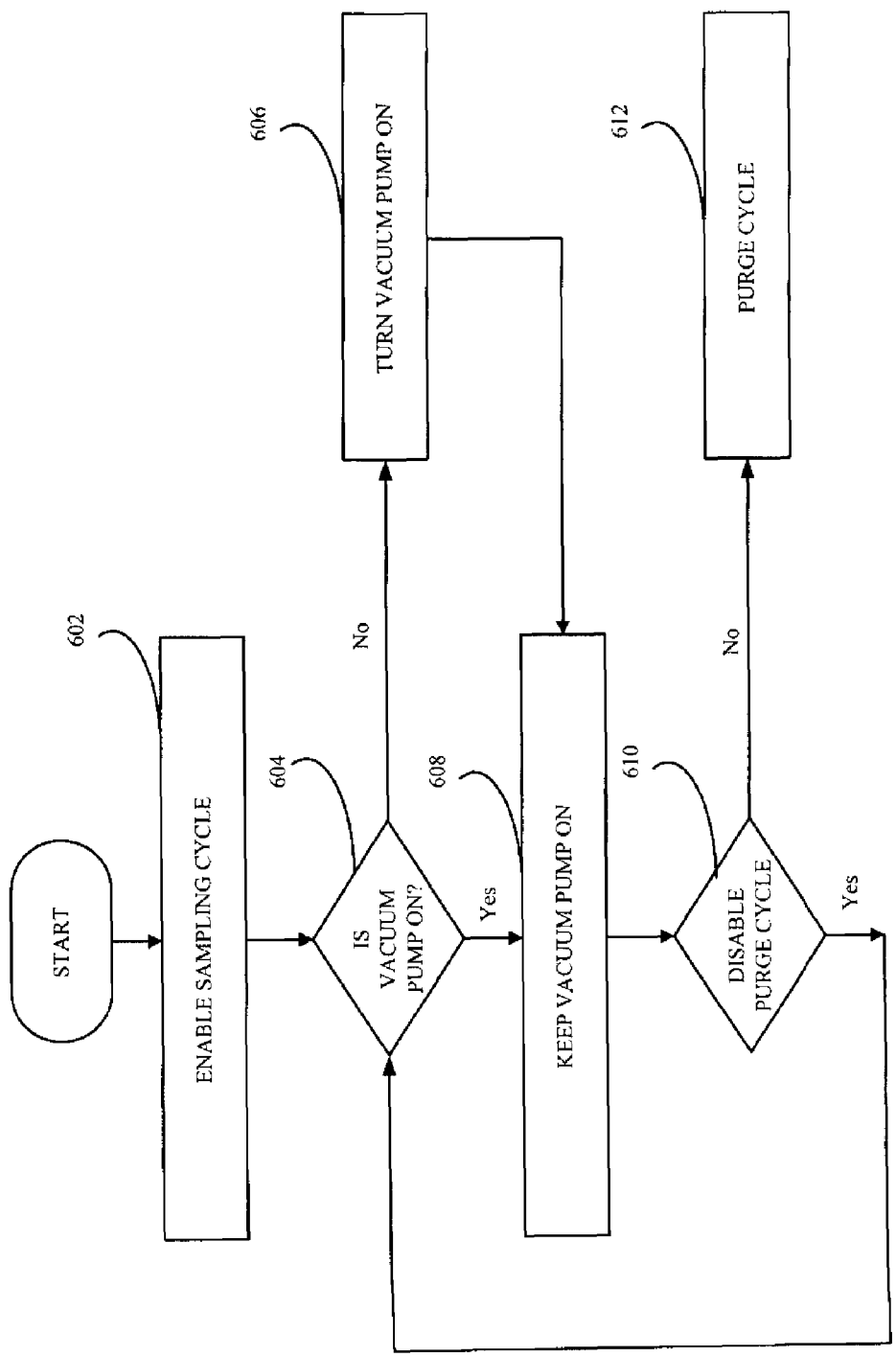
FIG. 6 is a process flow diagram illustrating isolator controller logic according to a non-limiting embodiment of the present invention.

FIG. 6 is a process flow diagram illustrating the isolator controller logic 600 according to one embodiment of the present invention. In step 602, the process enables the air sampling cycle, which is the normal operation of the sampling/monitoring system 200. In step 604, the isolator controller 504 checks if the vacuum pump 208 is on. If the vacuum pump 208 is on, then the purge pump 206 is necessarily off, because the isolator controller 504 can only enable the vacuum pump 208 or the purge pump 206 at any one time. If the vacuum pump 208 is not on, then the vacuum pump 208 is turned on in step 606. That can be accomplished automatically based on a preprogrammed time or operation, or manually by entering a command at the remote computing device 210 or at a touchpanel 214 located within the clean room 102.

In step 608, the isolator controller 504 keeps the vacuum pump 208 on. In step 610, the isolator controller 504 checks to see if the purge cycle should continue to be disabled. If so, the process returns to step 604 and the sampling cycle continues. Once the isolator controller 504 receives a signal from the controller 202 to enter the purge cycle, in step 612, the isolator controller 504 starts the purge cycle. At the end of the purge cycle, the isolator controller 504 returns to the air sampling cycle, at step 604, or possibly shuts off the system until the next air sampling system starts. In general, the purge cycle will run until the next air sampling cycle is scheduled, which could be, for example, once every 24 hours. In some clean rooms 102, such as a class 100 clean room, it may not be necessary to run a purge cycle during the period when the air sampling cycle is not being performed. The isolator controller logic 600 is implemented by an isolator printed circuit board (not shown) that interfaces with the SCADA (typically operated by a PC) or programmable logic controllers. The board eliminates the joining of the facility's 100 voltage system with the power system of the present invention.

The isolation circuit board is located in the controller 202 and can be connected to the SCADA or to a programmable logic controller system, such as that of the computing device 210. Accordingly, all commands and observations can be made at remotely. The wireless and isolation features of the system 200 can be implemented on any of the interfaces connected to the controller 202. For example, when the controller 202 receives a command to start an air sampling cycle, the touchpanel 214, the computing device 210, the inline flow control modules 904 (FIG. 9), and the digital flow enclosure 1602 (FIG. 16) will each observe the air sampling cycle in progress. Also for example, when an air flow error is detected, the controller 202 can broadcast the error detected in a particular port 308 to the touchpanel 214, the computing device 210, the inline flow control modules 904, and the digital flow enclosure 1602 (or any other input/output device connected to the system 200 that may be used).

The purging cycle involves injecting steam, hydrogen peroxide, or other vapor/gas into the air flow through the air sampling devices 216a, 216b, 216c, . . . , and 216n and air tubes 220. That may be accomplished by isolating the air sampling devices 216a, 216b, 216c, . . . , and 216n in one or more isolator chambers 514 and introducing a flow of purging gases at flow rate $Q_g$ into the chamber 514 when the purge cycle is turned on. The isolator chamber 514 does not have or allow any human contact inside the enclosure. Other techniques for purging and decontaminating air tubes are well known in the art. Users of the present system involved in pharmaceutical manufacturing operations will desire to sanitize various system components before any drug substances are mixed and before commencing with finish and fill operations. The purge mode of the present invention allows the sterilization of the tubes directly connected to the isolator. The purge vapor/gas exits the isolator controller 504. During the isolated purging cycle, the air flowing through the air tube 508 may be conditioned by gas conditioning device 516, which may comprise particulate filters (not shown), organic adsorbents, activated charcoal, a knockout drum, cyclone, or other substance or device, or combination of substances and devices.

Figure 7:
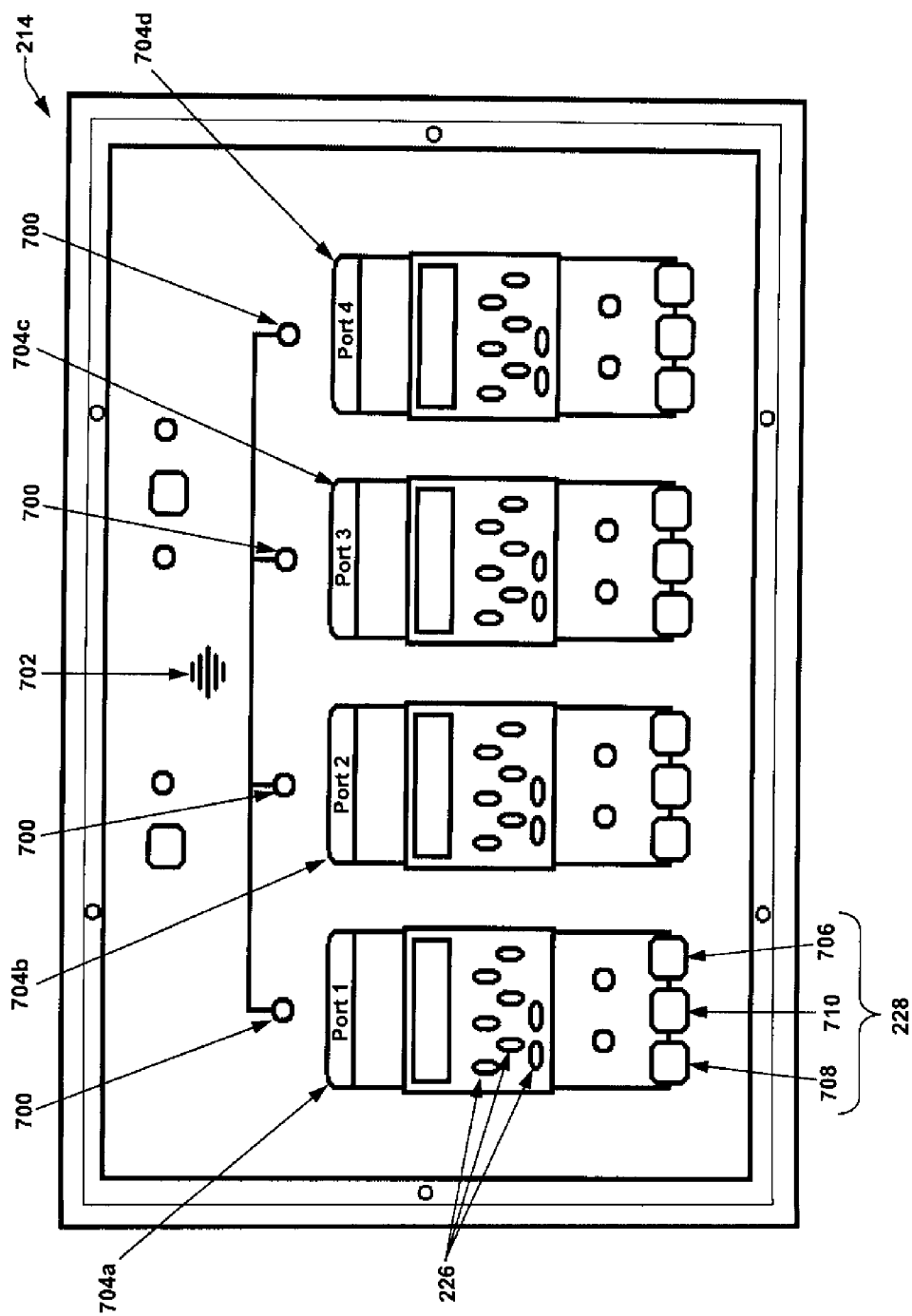
FIG. 7 is a detailed front view of a touchpanel according to a non-limiting embodiment of the present invention.

Turning now to FIG. 7, shown therein is a schematic diagram of a touchpanel 214 according to a non-limiting embodiment of the present invention. The touchpanel 214, as discussed previously, may be a static wall-mounted device, or it may be portable and adapted to being located on any flat surface, such as a bench, inside the working area of the clean room 102. The touchpanel 214 is the human interface input/output device for the air sampling/monitoring system 200. It remotely controls the controller 202 which is located outside the clean room 102. That design removes most of the electronics of the system from the aseptic areas of the clean room 102, including the system power supply, flow switch circuitry, and other electronics. The touchpanel 214 electronics are sealed inside the device so that the device may be disinfected like other portions of the clean room 102.

The touchpanel 214 allows the user to start, stop, program, and monitor whether and where air sampling and purge cycles are being performed within the clean room 102. It also allows the user to abort an air sampling cycle and to observe a visible alert indicator 700 and hear an audible alarm 702 if an airflow error is detected during an air sampling cycle. For example, an alert/alarm may be generated when the system detects a 1 CFM air flow error above or below the pre-programmed set-point flow rate. The visible alert indicator 700 may be a light-emitting diode (LED) that illuminates to provide a visible indication of the error to the user. And, the audible alarm 702 may be a buzzer that produces a sound to provide an audible indication of the error to the user. A start up/abort printed circuit board (not shown) controls the run and abort inputs of the timer 402 (see FIG. 4).

In the embodiment illustrated in FIG. 7, the touchpanel 214 includes four displays 704a, 704b, 704c, and 704d corresponding to each of four individual ports 308a, 308b, 308c, and 308d on the controller 202 connected to air sampling devices 216a, 216b, 216c, and 216d. But, just as controller 202 may have any number n of modular ports 308a, 308b, 308c, . . . , and 308n, the touchpanel 214 may have any number n of corresponding displays 704a, 704b, 704c, . . . , and 704n.

Each display 704a, 704b, 704c, and 704d includes various switches 228 for signaling to the controller 202 which air sampling devices 216a, 216b, 216c, and/or 216d to use for a sampling cycle. Those switches include a start switch 706, a stop switch 708, and an alarm reset switch 710. The start switch 706 powers up the touchpanel 214 and the individual ports 308a, 308b, 308c, . . . , and 308n of the controller 202 to which the touchpanel 214 is connected. One or more visual indicators 226, such as LEDs, provide a visual confirmation that the power on the touchpanel 214 has been activated and that the vacuum pump 208 is on. The air flow switch 404 at the controller 202 is adapted to accurately determine whether the vacuum pump is maintaining the proper flow rate at the corresponding port 308a, 308b, 308c, and 308d regardless of the composition of the flowing air (i.e., amount of nitrogen, argon, and carbon dioxide gases) so that status can be displayed at each corresponding display 704a, 704b, 704c, and 704d.

A start signal is input to the controller 202 from the touchpanel 214 when the start switch 706 is activated, which will initiate a sampling cycle in the controller 202 hardware. A start signal may also be sent from the timer 402 associated with one of the ports 308. When the individual ports 308a, 308b, 308c, and 308d of the controller 202 receive the start signal, the controller 202 will start a sampling cycle by controlling the isolator controller 504. The controller 202 then informs the touchpanel 214 that a sampling cycle instruction signal has been issued.

Activating the stop switch 708 sends an abort signal to the controller 202 that halts a sampling cycle already in progress. When the individual ports 308a, 308b, 308c, and 308d of the controller 202 receive the abort signal, the controller 202 will instruct the touchpanel 214 by controlling the isolator controller 504. The controller 202 then informs the touchpanel 214 that the sampling cycle instruction signal has been halted. When a sampling cycle is in progress, the individual ports 308a, 308b, 308c, and 308d of the controller 202 will instruct the touchpanel 214 and, if necessary, the SCADA interface 410 (e.g., to communicate with a separate system), that a sampling cycle is in progress. That signal will remain active for the remainder of the sampling cycle duration.

When an individual port 308a, 308b, 308c, . . . , or 308n is in the middle of a sampling cycle and an air flow deficiency is detected, the controller 202 will broadcast a 1 CFM error to the port 308a, 308b, 308c, . . . , or 308n that is in the middle of the sampling cycle. The power input to the SCADA system will go from active to non-active during a sampling cycle for that port 308a, 308b, 308c, . . . , or 308n and continue to be non-active for the duration of the sampling cycle, or until the 1 CFM error is removed. Activating the alarm reset switch 710 manually resets (i.e., turns off) the visual alert indicator 700 for each individual display 704a, 704b, 704c, or 704d if a 1 CFM error occurs at that the corresponding port 308a, 308b, 308c, or 308d during a sampling cycle.

Each touchpanel 214 can include its own power source, such as an independent DC power supply (i.e., batteries), or it can be electrically connected and powered by the controller 202 via signal wires 218 (FIG. 2) that provide DC power to the touchpanel 214. In the latter configuration, the signal wires 218 are shielded plenum wire configured to transmit less than about 2 watts of power.

The touchpanel 214 either includes signal wires 218 (FIG. 2) or utilizes a wireless connection to communicate signals with the ports 308a, 308b, 308c, . . . , and 308n of the controller 202. The touchpanel 214 may include a different signal wire 218a, 218b, 218c, . . . , or 218n or paired wireless connection for each of the individual ports 308a, 308b, 308c, . . . , and 308n of the controller 202. Accordingly, the number n of signal wires 218a, 218b, 218c, . . . , and 218n or paired wireless connections connecting the touchpanel 214 to the individual ports 308a, 308b, 308c, . . . , and 308n of the controller 202 will depend on the number n of ports the touchpanel 214 is controlling.

Figure 8:
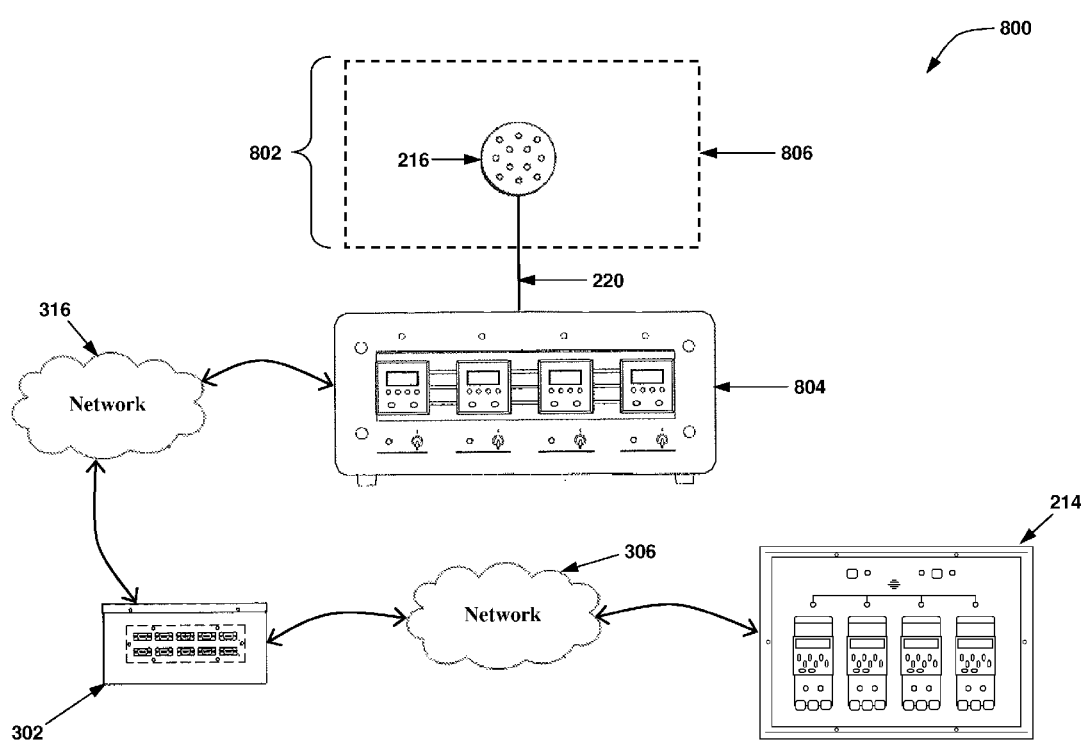
FIG. 8 is a schematic diagram of an air sampling/monitoring system for use in the clean room of FIG. 1 according to another non-limiting embodiment of the present invention.

Turning now to FIG. 8, shown therein is a schematic diagram of a portable air sampling/monitoring system 800 according to another non-limiting embodiment of the present invention. The air sampling/monitoring system 800 includes a filtered sampling device 802, a controller 804 (front view shown), a touchpanel 214, and a touchpanel base station 302. Although the computing device 210 is not illustrated, that component may also be present in the sampling/monitoring system 800 as described above for the sampling/monitoring system 200 illustrated in FIG. 2.

The filtered sampling device 802 includes an air sampling device 206 located within a laminar air flow hood or isolation chamber 806, which may include a high efficiency particulate air (HEPA) filter (not shown). The air sampling device 206 and the controller 804 are provided in a single, portable filtered sampling device 802 that may be placed in any location within the clean room 102, or outside the clean room 102, as necessary.

The air sampling device 206 is attached to the controller 804 using a vacuum air tube 220 that is about seven feet or less. The features and functionality of the controller 804 are similar to those described above in connection with FIGS. 2-5. For example, the controller 804 provides for a 1 CFM air flow error detection during an air sampling cycle and it is easily connected to a facilities' 100 SCADA. The controller 804 differs from the controller 202 illustrated in FIGS. 2-5 primarily in that it includes a self-contained vacuum pump (not shown) rather than an external air vacuum pump 208, as illustrated most clearly in FIGS. 2 and 5.

The touchpanel base station 302 is preferably positioned at a location near the controller 804 and is configured to route signals between the controller 804 and the touchpanel 214, either by signal wires 304 and 314, wireless network 306 and 316, or a combination thereof. In the portable air sampling/monitoring system 800 illustrated in FIG. 8, the system is entirely wireless such that the touchpanel base station 302 routes signals wirelessly between the controller 804 and the touchpanel 214 via wireless network 306 and 316. In addition, the touchpanel 214 is portable rather than wall-mountable in that embodiment, which provides the user with portable input/output control of the air sampling device 206 by way of the controller 804. Accordingly, the portable air sampling/monitoring system 800 illustrated in FIG. 8 is fully portable and does not require any penetration of walls, ceilings, or floors for installing wall-mounted components or routing cables or air tubes. For example, the filtered sampling device 802 and the controller 804 may be placed in a clean room 102 and monitored and controlled remotely using the touchpanel 214 in an adjacent space 104. The touchpanel base station 302 may be positioned at any point in between the controller 804 and the touchpanel 214 as required to facilitate signal routing therebetween. Thus, the installation costs are much less than other embodiments described previously.

Figure 9:
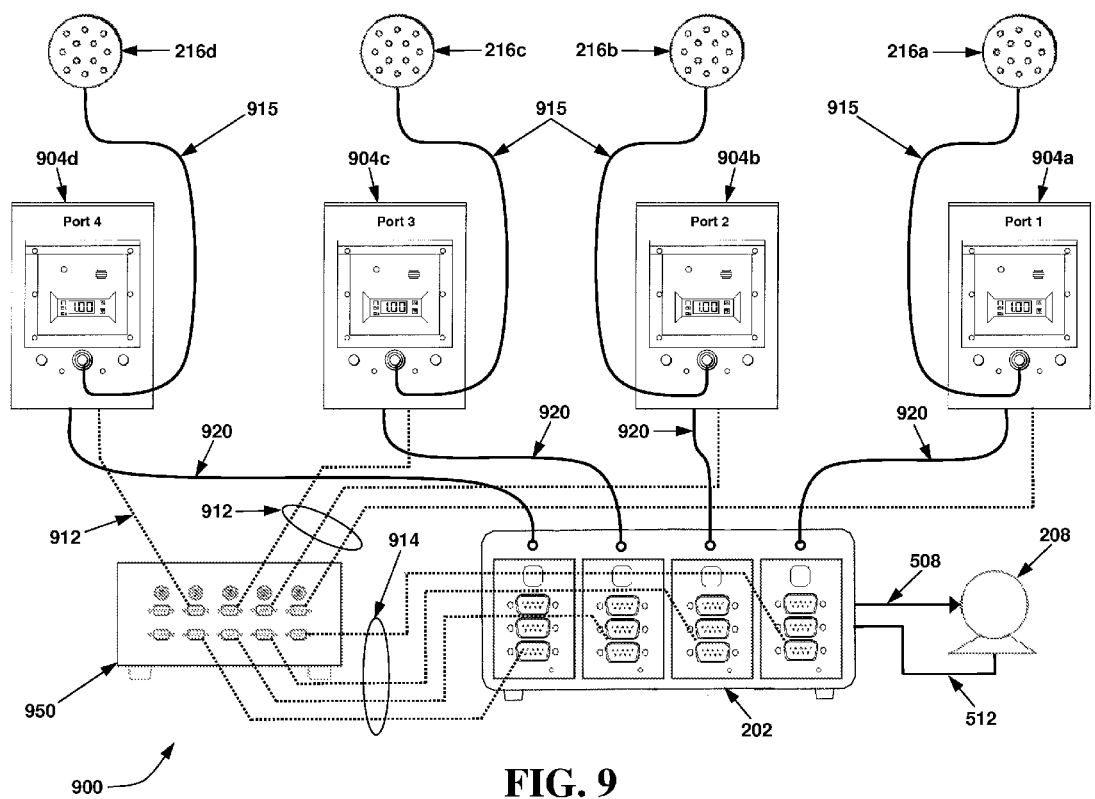
FIG. 9 is a schematic diagram of an air sampling/monitoring system for use in the clean room of FIG. 1 according to yet another non-limiting embodiment of the present invention.

Referring to FIG. 9, a sampling/monitoring system 900 is shown in accordance with an yet another non-limiting embodiment of the present invention. The system 900 includes a controller 202 (rear view shown), four inline flow control modules 904a, 904b, 904c, and 904d, an inline flow control base station 950, four air sampling devices 216a, 216b, 216c, and 216d, and a vacuum pump 208. Although the computing device 210 is not illustrated, that component may also be present in the sampling/monitoring system 900 as described above for the sampling/monitoring system 200 illustrated in FIG. 2. And, although only four inline flow control modules 904a, 904b, 904c, and 904d and air sampling devices 216a, 216b, 216c, and 216d are illustrated, any number n of inline flow control modules 904a, 904b, 904c, ..., and 904n and four air sampling devices 216a, 216b, 216c, ..., 216n may be used.

The features and functionality of the controller 202 are substantially the same as those described above in connection with FIGS. 2-5 and utilizes an external vacuum pump 208. The controller 202 communicates with the inline flow control modules 904a, 904b, 904c, and 904d by way of the inline flow control base station 950 to control operation of the inline flow control modules 904a, 904b, 904c, and 904d. The flow rate at each individual air sampling device 216a, 216b, 216c, or 216d will be measured and displayed at the corresponding inline flow control module 904a, 904b, 904c, or 904d so those flow rates can be monitored independently at each inline flow control module 904a, 904b, 904c, or 904d. A flow alert/alarm is generated in the event that the flow rate measured at any individual inline flow control module 904a, 904b, 904c, or 904d is outside of a desired flow rate. Accordingly, the sampling/monitoring system 900 illustrated in FIG. 9 allows the sampling cycle occurring at each individual sampling device 216a, 216b, 216c, and 216d to be monitored and controlled independently of one another, thereby adding an additional degree of freedom of operation to the present invention.

As shown, a separate inline flow control module 904a, 904b, 904c, or 904d is associated with each air sampling device 216a, 216b, 216c, or 216d. Each air sampling device 216a, 216b, 216c, or 216d is connected to its respective inline flow control module 904a, 904b, 904c, and 904d by an atrium air flow line 915, and each inline flow control module 904a, 904b, 904c, and 904d is connected to the controller 202 by a vacuum air line 920. The vacuum pump 208 is connected to the controller 202 by air tube 508. The controller 202 separates the air flow created by the vacuum pump 208 among the various vacuum air lines 920 leading out from the controller 202 to the inline flow control modules 904a, 904b, 904c, and 904d. The vacuum pump 208 is in fluid communication with a manifold that connects the vacuum pump 208 to the proper solenoid to direct the air flow to one or more desired vacuum air lines 920. The controller 202 is configured so that each atrium air flow line 915 and vacuum air line 920 carries 1 CFM of air, which is the desired air flow rate needed to conduct a proper sampling cycle at the air sampling devices 216a, 216b, 216c, and 216d. By way of comparison, the various air sampling devices 216a, 216b, 216c, and 216d in the embodiment illustrated in FIG. 2 were in direct flow communication with the controller 202 via the air tubes 220, while the inline flow control modules 904a, 904b, 904c, and 904d are positioned between the air sampling devices 916 and the controller 202 in the embodiment illustrated FIG. 9.

In addition, the inline flow control modules 904a, 904b, 904c, and 904d are in electrical communication with the inline flow control base station 950 via a first group of signal wires 912. The inline flow control base station 950 is in electrical communication with the controller 202 via a second group of signal wires 914. Separate signal wires 912 are provided for each inline flow control module 904a, 904b, 904c, and 904d and respective air sampling device 216a, 216b, 216c, or 216d. As shown, the vacuum air lines 920 and signal wires 914 are connected at respective ports 308a, 308b, 308c, and 308d of the controller 202, which are illustrated more clearly in FIG. 3. The ports 308a, 308b, 308c, and 308d are dedicated to the respective inline flow control modules 904a, 904b, 904c, and 904d and not shared with any other ports. Although the controller 202, the inline flow control base station 950, and the inline flow control modules 904a, 904b, 904c, and 904d are shown in wired communication with one another, it should be appreciated that those components of the sampling/monitoring system 900 can also be in wireless communication, as described for the various embodiments above. Accordingly, the controller 202 activates the various ports 308a, 308b, 308c, and 308d, which activate a respective inline flow control module 904a, 904b, 904c, or 904d.

The various inline flow control modules 904a, 904b, 904c, and 904d are shown connected in a parallel manner to the controller 202 and to the inline flow control base station 950. It should be apparent, however, that the controller 202, the inline flow control base station 950, and the inline flow control modules 904a, 904b, 904c, and 904d can be connected in any suitable manner. For example, the inline flow control modules 904a, 904b, 904c, and 904d can have identification codes, and the controller 202 can communicate with the different inline flow control modules 904a, 904b, 904c, and 904d by use of those ID codes via a common connection (e.g. a single signal wire). And, because each of the components is connected in series, certain intermediate components may be removed or incorporated into other components. For example, the inline flow control modules 904a, 904b, 904c, and 904d can be directly connected to the controller 202 so that an inline flow control base station 950 need not be utilized.

The vacuum pump 208 receives its power from the controller 202 via the signal wire 512 that provides an electrical connection with the controller 202. The controller 202 has an AC power supply 406 (FIG. 4) that supplies power to various components of the sampling/monitoring system 900, including the inline flow control modules 904a, 904b, 904c, and 904d. The inline flow control base station 950 also has an AC power supply 1406 (FIG. 14) that supplies its power. It will be appreciated, however, that each of the components of the sampling/monitoring system 900 can have its own power source or can be powered via an electrical connection with the controller 202, as conditions permit or require.

The inline flow control modules 904a, 904b, 904c, and 904d monitor the actual flow rate that is realized at each respective air sampling device 216a, 216b, 216c, and 216d. If the flow rate on the vacuum air line 920 is off by ±5% (i.e., not within the range of 0.95-1.05 CFM), then the corresponding inline flow control module 904a, 904b, 904c, or 904d generates an alarm signal. However, the sampling cycle continues until the user decides to abort the sampling cycle. Preferably, each inline flow control module 904a, 904b, 904c, and 904d includes an 8 second delay before the alarm signal is generated. That delay accounts for fluctuations that may occur during initial start-up of the system 900. A typical sampling cycle may last between 10 minutes and 3 hours.

In addition, it should be appreciated that each inline flow control module 904a, 904b, 904c, and 904d can optionally transmit the alarm signal to the inline flow control base station 950, which can then send an alarm signal back to the other inline flow control modules 904a, 904b, 904c, and/or 904d to activate their respective visual alert indicators 1004 and audible alarms 1006.

The inline flow control base station 950 also sends a flow switch disconnect signal to the controller 202 over the signal wire 914 in response to the user manually activating a stop switch 1000 (FIG. 10) on an inline flow control module 904*a*, 904*b*, 904*c*, or 904*d*. In response to the disconnect signal, the controller 202 cuts off the flow of air to the respective inline flow control module 904*a*, 904*b*, 904*c*, or 904*d*.

Figure 10:
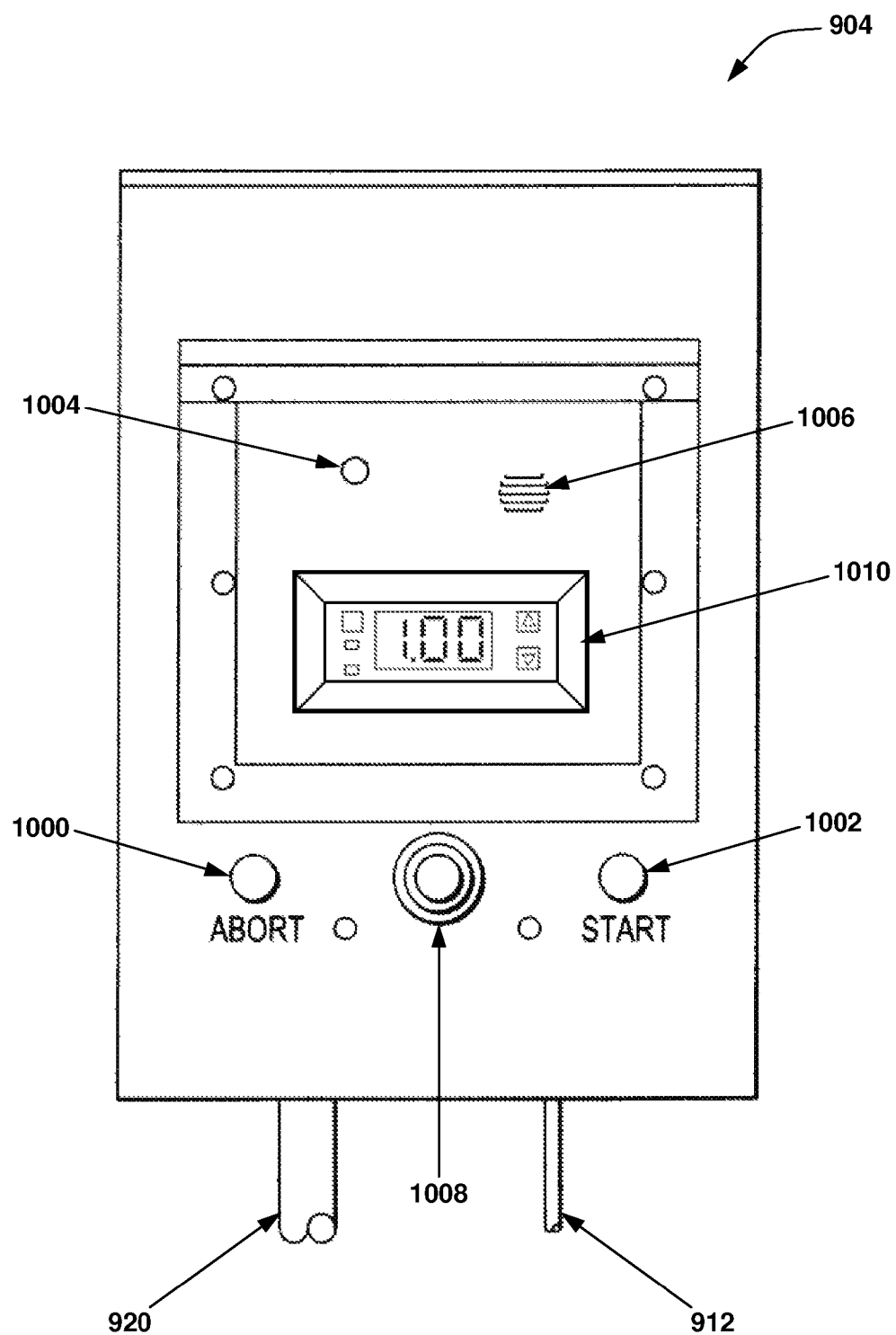
FIG. 10 is a detailed front view of an inline flow control module according to a non-limiting embodiment of the present invention.

Turning to FIG. 10, an inline flow control module 904 is shown in greater detail with its corresponding vacuum air line 920 and signal wire 912. The inline flow control module 904 has a stop switch 1000, a start switch 1002, dual alert/alarm indicators 1004 (visual) and 1006 (audible), an air flow plug adapter 1008, and a display interface 1010. The start switch 1002 is used to manually activate a sample period. In response to the start switch 1002 being activated, the inline flow control module 904 sends a signal to the controller 202 via the flow base station 950. The controller 202 activates the vacuum pump 208 to cause the air flow on the vacuum air line 920 to the respective air sampling device 216*a*, 216*b*, 216*c*, or 216*d* via the atrium air flow line 915.

The stop switch 1000 aborts the sampling cycle and turns off the vacuum air flow for the corresponding air sampling device 216. When the stop switch 1000 is activated, a stop signal is sent to the controller 202 via the inline flow control base station 950. In response, the controller 202 turns off the vacuum pump 208 to the respective inline flow control module 904. The user may abort the sampling cycle for various reasons, including that an alert/alarm has been signaled by an inline flow control module 904.

The alert/alarm indicators 1004 and 1006 indicate if the air flow at the inline flow control module 904 is out of specification (e.g., not within the range of 0.95-1.05 CFM). Both a visual alert indicator 1004, such as an LED, and an audible alarm 1006, such as a buzzer, are provided to alert the user when the flow rate is out of specification. The alert and alarm continue until the stop switch 1000 is activated, or the error conditions are removed, and the flow rate returns to the desired level (e.g., 1 CFM).

Thus, in accordance with the embodiment illustrated in FIG. 9, the air flow is only activated and de-activated when the user manually operates the stop and start switches 1000 and 1002, respectively. And, the stop and start switches 1000 and 1002 only activate and de-activate the air flow for the particular inline flow control module 904 at which the user manually operates those switches 1000 and 1002. That way, the user can verify that the air sampling device 216 associated with that inline flow control module 904 is properly set up and ready to perform a sampling cycle. However, it should be appreciated that the system can be configured so that the user can start and stop air flow to other or all of the inline flow control modules 904*a*, 904*b*, 904*c*, . . . , and 904*n* in the sampling/monitoring system 900, either simultaneously or at other times, at any of the inline flow control modules 904*a*, 904*b*, 904*c*, . . . , and 904*n*, or at either the controller 202 or the inline flow control base station 950.

Figure 11:
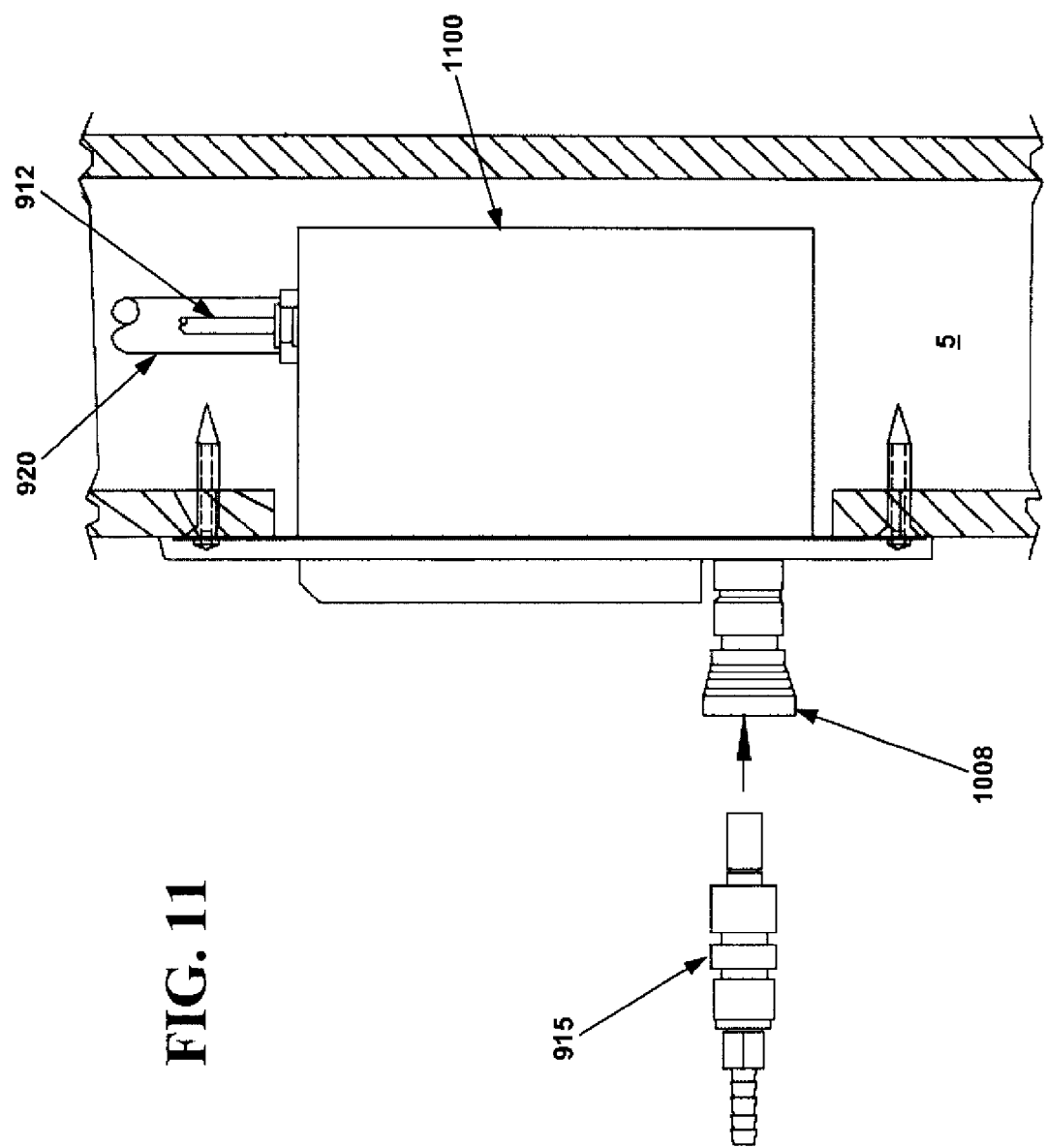
FIG. 11 is a detailed side view of the inline flow control module shown in FIG. 10.

An air flow plug adapter 1008 is provided on the front face of the inline flow control module 904. As FIG. 11 illustrates, the plug adapter 1008 is adapted to connect to the atrium air flow line 915. The plug adapter 1008 is preferably a quick disconnect so that the atrium air flow line 915 can be quickly connected and disconnected and replaced, if necessary. As further illustrated in FIG. 11, the inline flow control module 904 can be contained within a housing 1100 and mounted either internal to a wall 5, as shown, or externally on the face of the wall 5. The electronics of the inline flow control module 904 may be sealed inside the housing so that the device may be disinfected like other portions of the clean room 102.

Figure 12:
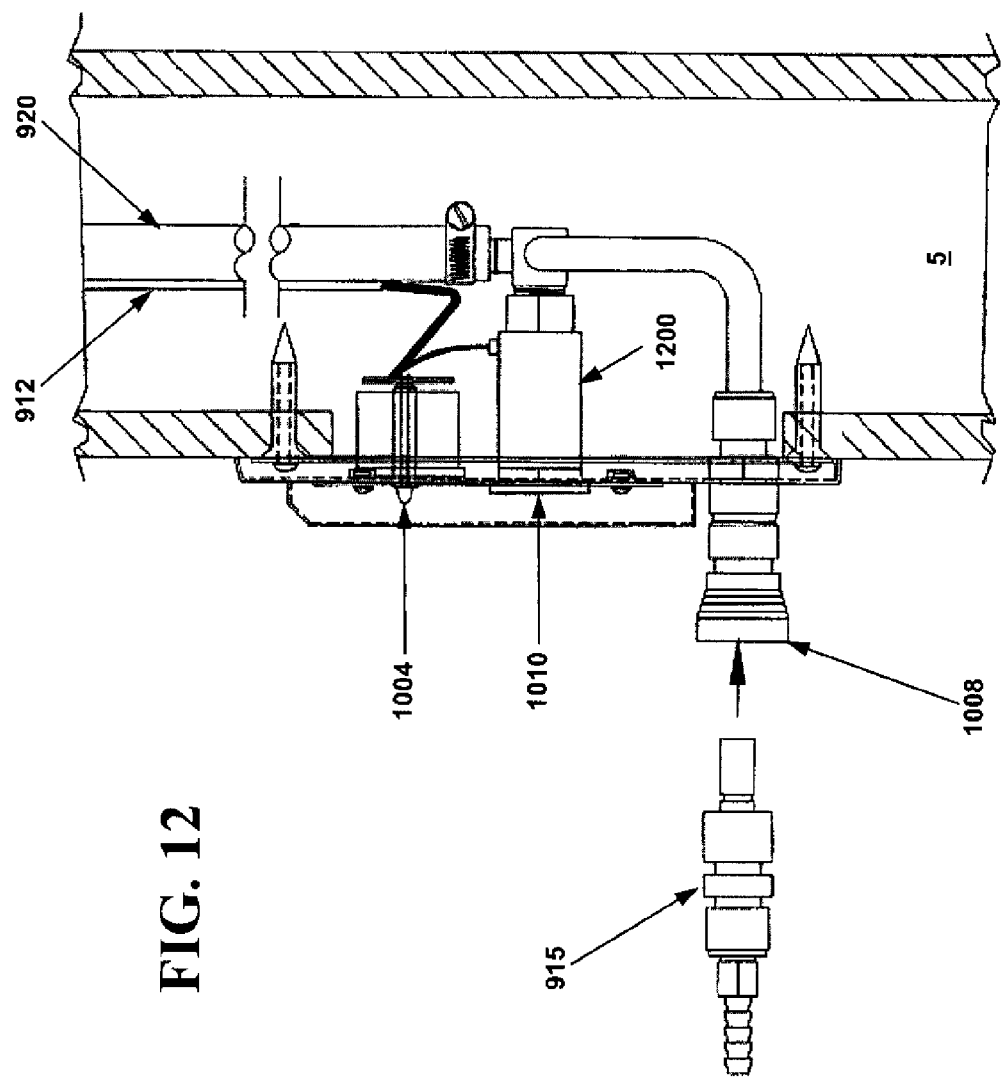
FIG. 12 is another detailed side view of the inline flow control module shown in FIG. 10 with the housing removed.
Figure 13A:
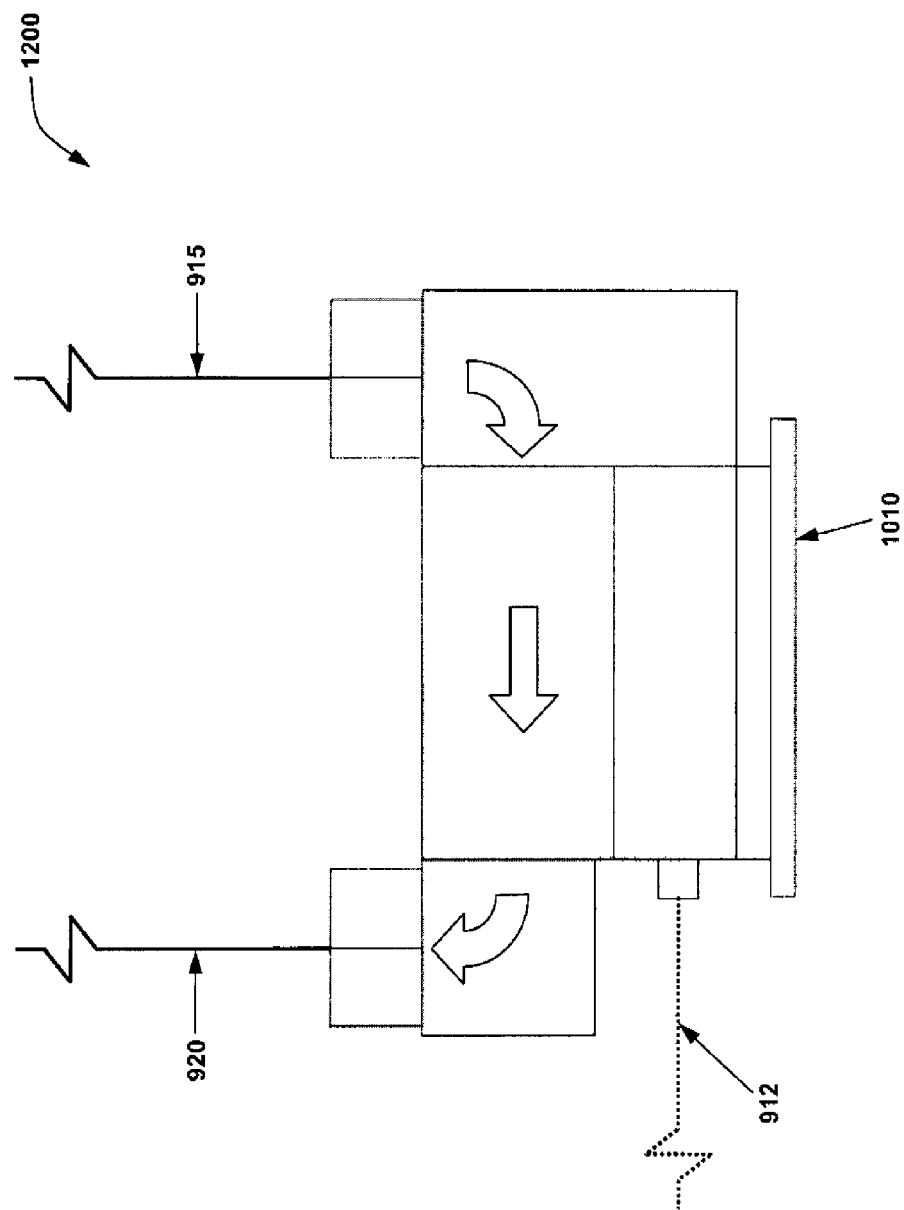
FIG. 13A is a top view of a digital flow switch used in the inline flow control module shown in FIG. 12 according to a non-limiting embodiment of the present invention.

Referring to FIG. 12, the inline flow control module 904 is shown with the housing 1100 removed to show the internal workings, including a digital flow switch 1200. The vacuum line 920 connects through to the plug adapter 1008 for easy connection to the atrium air flow line 915. As illustrated in more detail in FIG. 13A, one end of the digital flow switch 1200 is connected to the vacuum air line 920 and the opposite end is connected to the atrium air flow line 915, which leads to an air sampling device 216. The digital flow switch 1200 detects the flow rate coming in from the atrium air flow line 915 and passing through to the vacuum air line 920. The digital flow switch 1200 generates an alarm signal if the detected air flow rate is not within the parameters set by the user. If an alarm signal is generated, the alert/alarm indicators 1004 and 1006 are activated. Accordingly, the signal wire 912 is connected to a data port on the digital flow switch 1200 (FIGS. 12 and 13A) and to the alert/alarm indicators 1004 and 1006. In addition, the detection performed by the digital flow switch 1200 at each inline flow control module 904*a*, 904*b*, 904*c*, . . . , and 904*n* is independent of the flow rate detection performed by the air flow switch 404 at the controller 202 so that the flow rate is simultaneously monitored at two locations during a sampling cycle.

The inline flow control module 904 is preferably positioned near its respective air sampling device 216 in the clean room, whereas the controller 202 is remotely located outside the clean room 102. In accordance with the embodiment illustrated in FIG. 9, the atrium air flow line 915 is from about 1-20 feet in length so that the inline flow control module 904 can be located in the clean room 102 with the air sampling device 916. Locating the inline flow control module 904, and therefore the digital flow switch 1200, near the sampling device 216 ensures that the flow rate at the air sampling devices 916 is accurate and allows problems with the sampling cycle taking place at any individual air sampling device 216*a*, 216*b*, 216*c*, . . . , or 216*n* to be quickly and easily identified, isolated, and corrected. Moreover, because each air sampling device 216*a*, 216*b*, 216*c*, . . . , and 216*n* may have its own corresponding inline flow control module 904*a*, 904*b*, 904*c*, . . . , and 904*n*, those problems can be identified, isolated, and corrected without the need to interfere with the operation of any other air sampling device 216*a*, 216*b*, 216*c*, . . . , and 216*n*.

For example, the digital flow switch 1200 will identify an error in the flow rate from an individual sampling device 216 due to a break in the vacuum air line 920 between the controller 202 and the inline flow control module 904, which is particularly advantageous when the vacuum air line 920 is within a wall 5 or near noisy equipment such that a break would otherwise be difficult to detect. The digital flow switch 1200 will also identify an error in the flow rate from an individual sampling device 216 where either the atrium air flow line 915 or vacuum air line 920 is kinked or not properly connected. And, the digital flow switch 1200 will identify if the vacuum pump 208 is not turned on or working properly. When identified, such problems can be corrected without affecting any other sampling devices 216*a*, 216*b*, 216*c*, . . . , and 216*n*.

Figure 13B:
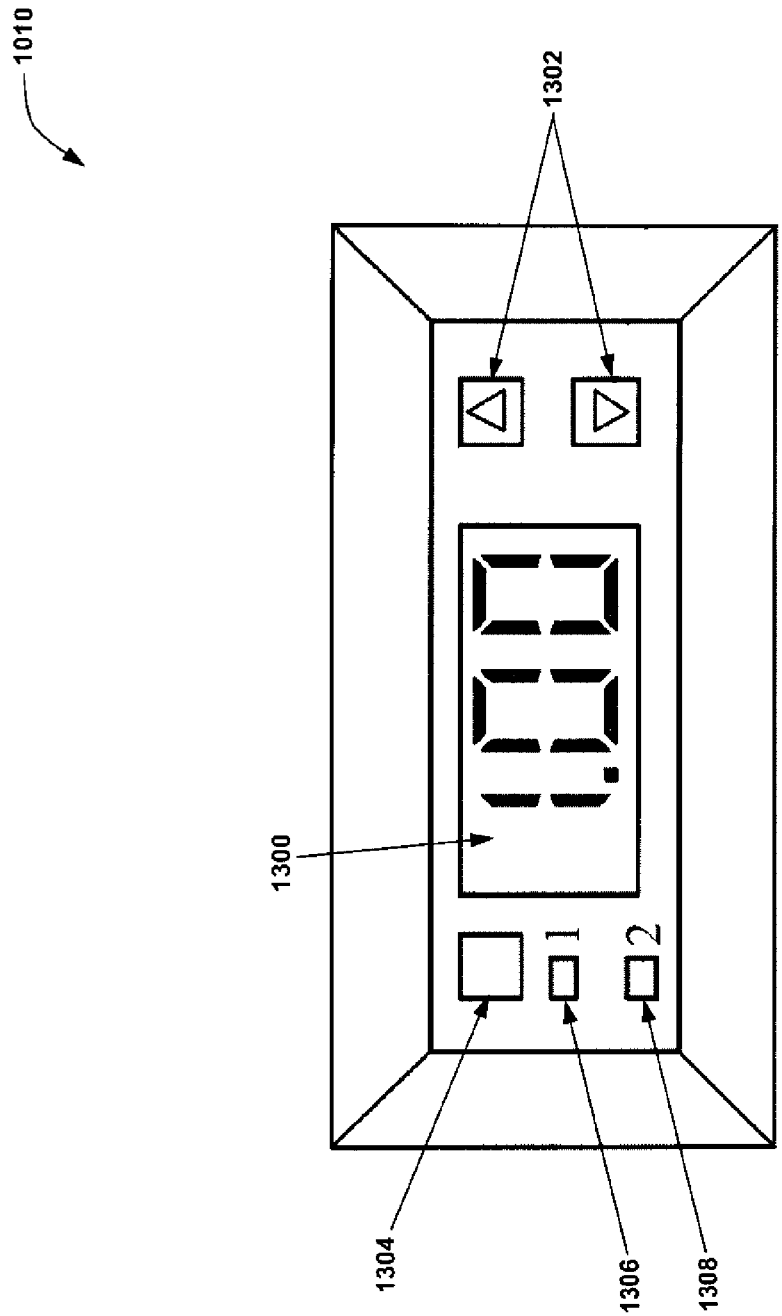
FIG. 13B is a detailed front view of the display interface of the inline flow control module shown in FIG. 10 and the digital flow enclosure shown in FIG. 17 according to a non-limiting embodiment of the present invention.

Turning to FIG. 13B, the display interface 1010 of the inline flow control module 904 is shown in further detail. The display interface 1010 includes a digital LED display 1300 that, unlike conventional rotameters, can be read from multiple angles and distances. The display interface 1010 has various buttons 1302-1308 that allow the user to set the desired range of flow rates. That functionality is not provided in the touchpanel 214 described above. If the detected flow rate is outside of the range set with those buttons, the alarm signal is generated. In FIG. 13B, the desired flow rate of 1.00 CFM is shown on the display interface 1010. That rate can be changed by pressing the up/down arrows 1302 to increase or decrease the value that is displayed, which is then transmitted to the controller 202 so that the desired flow rate being displayed is provided via the vacuum air line 920. The inline flow control module 904 can be calibrated and is accurate to a flow rate of ±5 percent of 1 CFM.

The display interface 1010 also has a programming button 1304 to further assist the user (e.g., a technician on site or the manufacturer) set the desired flow rate and other display options, such as whether to display values in CFM or LPM. Light indicators 1306 and 1308 are provided as an easy reference for the user to confirm that the inline flow control module 904 is operating properly and that the flow rate is being detected. For example, one light 1306 can indicate that the flow rate is above the minimum desired value (i.e., 0.95 CFM) and the other light 1308 can indicate that the flow rate is below the maximum desired value (i.e., 1.05 CFM). During a sampling cycle, the air flow rate measured by the digital flow switch 1200 is displayed so that the user can observe that the correct air flow is within specification and confirm that air is flowing properly at the respective sampling device 216.

In addition, the user can observe that the respective port 308a, 308b, 308c, . . . , or 3087n of the controller 202 is activated and that the respective inline flow control module 904a, 904b, 904c, . . . , or 904n is plugged into the inline flow control base station 950, which results in the display interface 1010 being activated. Under normal operating conditions, the flow rate detected by the controller 202 should be the same as that detected by the inline flow control module 904 and displayed on the display interface 1010. If either one of those flow rates drops below or rises above the desired flow rate, the alert/alarm indicators 1004 and 1006 will be activated at the inline flow control module 904, thereby providing two points of measurement to ensure the desired flow rate is maintained at each sampling device 216a, 216b, 216c, . . . , and 216n in the sampling/monitoring system 900. That redundancy further helps the user to quickly and accurately identify, isolate, and correct problems with a sampling cycle at any individual sampling device 216a, 216b, 216c, . . . , or 216n, regardless of the conditions at the other sampling devices 216a, 216b, 216c, . . . , and 216n.

Figure 14:
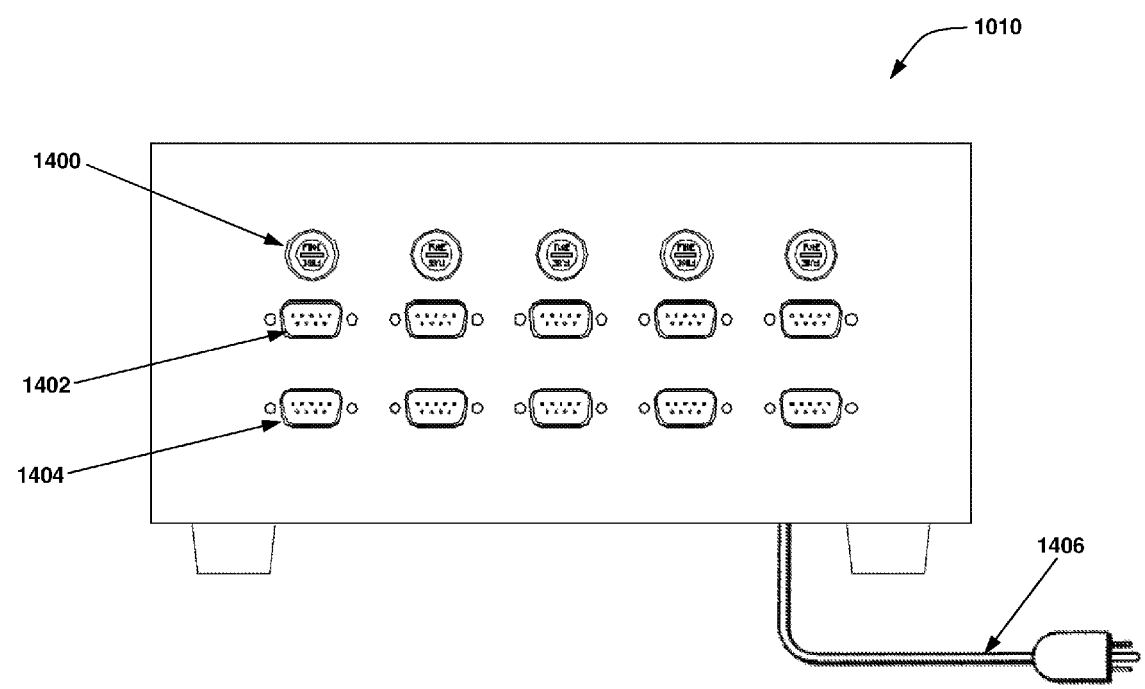
FIG. 14 is a rear view of an inline flow control base station used with air sampling/monitoring system shown in FIG. 9 according to a non-limiting embodiment of the present invention.

As shown in FIG. 14, the inline flow control base station 950 has a row of amps 1400, a row of inputs 1402, a row of outputs 1404, and an AC power supply 1406. The rows are aligned so that each column contains a single amp 1400, input 1402, and output 1404 associated with each individual inline flow control module 904. The inputs 1402 receive the signal wire 912 from the inline flow control module 904 and the outputs 1404 connect to the signal wire 914 leading to the controller 202. The inputs 1402 also provide power to their respective inline flow control module 904 to power that inline flow control module 904. The AC power supply 1406 supplies power to the inline flow control base station 950. The inline flow control base station 950 is preferably located outside of the clean room 102 in an adjacent room 104 and/or with the controller 202. The sampling/monitoring system 900 is modular, so any number n of inline flow control modules 904a, 904b, 904c, . . . , and 904n can be plugged into the inline flow control base station 950 as needed for a particular application.

The inline flow control base station 950 isolates the inline flow control modules 904a, 904b, 904c, and 904d from the controller 202. Thus, the DC voltage and logic signals connected to the inline flow control modules 904a, 904b, 904c, and 904d are isolated from the controller 202. That is done so that a short in the controller 202 does not cause a short in any of the inline flow control modules 904a, 904b, 904c, and 904d so the inline flow control modules 904a, 904b, 904c, and 904d can then be controlled by another device. The inline flow control modules 904a, 904b, 904c, and 904d are modular and electrically isolated from the controller's 202 DC voltage and ground distribution system. Accordingly, the inline flow control base station 950 is effectively a repeater that passes signals between the inline flow control modules 904a, 904b, 904c, and 904d and the controller 202, that generates the DC voltage needed by the inline flow control modules 904a, 904b, 904c, and 904d, and that electrically isolates the controller 202.

In addition, the sampling/monitoring system 900 shown in FIG. 9 can be used with a touchpanel 214 in a similar manner as described for the sampling/monitoring system 200 shown in FIG. 2. The touchpanel 214 can be connected by wire or wirelessly. In that configuration, the inline flow control module 904 would remain positioned between each air sampling device 216 and the controller 202, along air tube 220. In the alternative, the touchpanel 214 and its operations can be a separate device, or integrated into one or more of the inline flow control modules 904a, 904b, 904c, . . . , and 904n.

Figure 15:
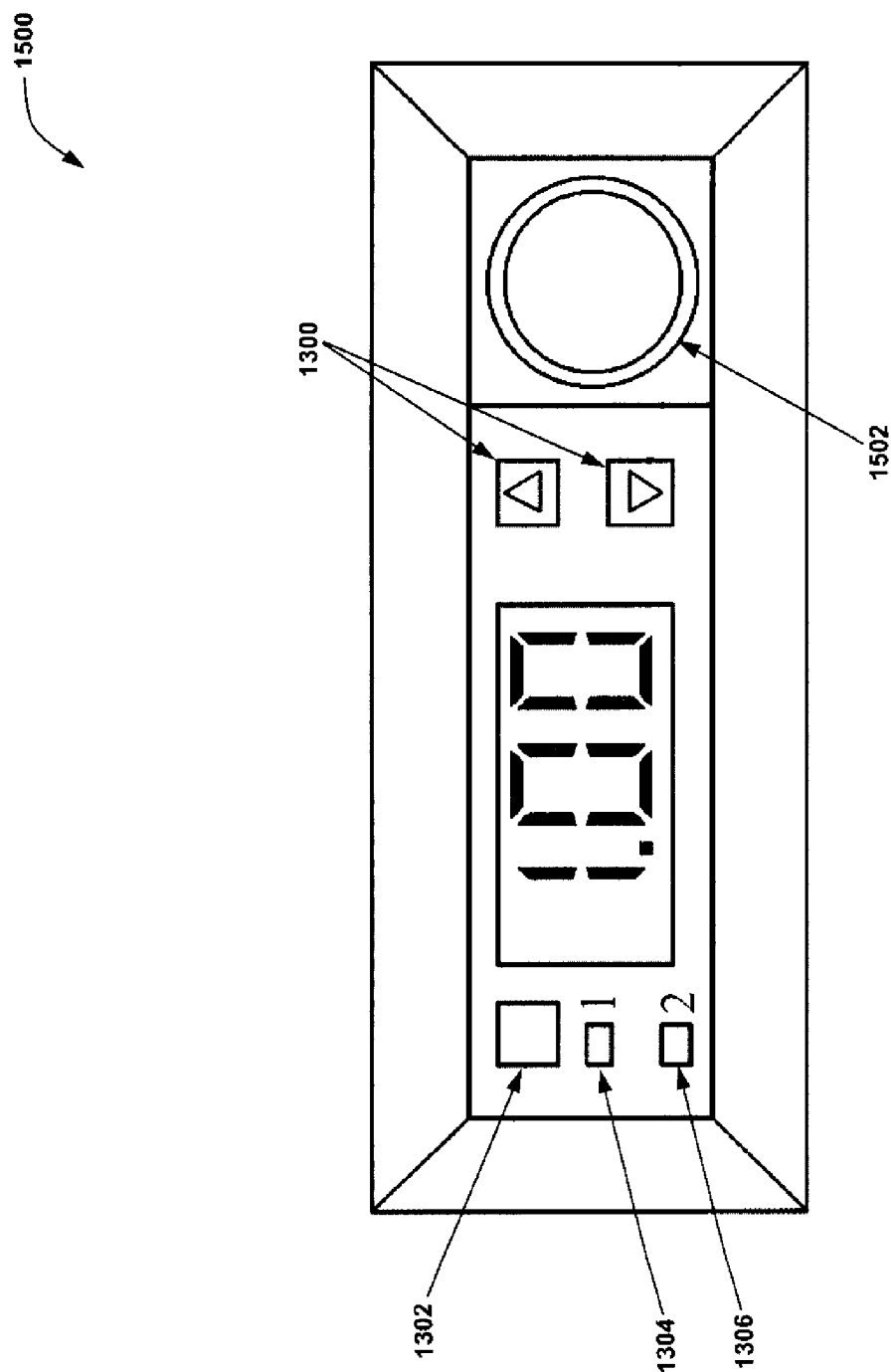
FIG. 15 is a detailed front view of a display interface of a controller in accordance with a non-limiting embodiment of the present invention.

Referring to FIG. 15, the display interface 1500 of the controller 202 is shown. The display interface 1500 of controller 202 is used to operate the flow rate detection at the controller 202. It has similar control buttons as the display interface 1010 of the inline flow control module 904 illustrated in FIG. 13B. However, the display interface 1500 of the controller 202 also has a flow control knob or pinch valve 1502. The flow control knob 1502 allows the user to manually adjust the air flow rate through the vacuum air lines 920. The air flow rate may need to be adjusted depending on several factors, such as the length of the vacuum air line 920 and the number n of inline flow control modules 904a, 904b, 904c, . . . , and 904n that are activated at any one time.

Referring to FIG. 16, a sampling/monitoring system 1600 is shown in accordance with yet another non-limiting embodiment of the present invention. The system 1600 includes a controller 202 (bottom view shown), a digital flow enclosure 1602 (rear view shown), a controller base station 1604, an flow enclosure base station 1606, four air sampling devices 216a, 216b, 216c, and 216d, a vacuum pump 208 (not shown), and a touchpanel 214. Although the computing device 210 is not illustrated, that component may also be present in the sampling/monitoring system 1600 as described above for the sampling/monitoring system 200 illustrated in FIG. 2. And, although only four air sampling devices 216a, 216b, 216c, and 216d are illustrated, any number n of air sampling devices 216a, 216b, 216c, . . . , 216n and corresponding components may be used.

The features and functionality of the controller 202 and touchpanel 214 are substantially the same as those described above in connection with FIGS. 2-8. The controller 202 communicates with the controller base station 1604, which wirelessly communicates with the flow enclosure base station 1606 via a communications network 1608, to control the operation of the digital flow enclosure 1602. The controller base station 1604 and the flow enclosure base station 1606 may each include an internal receiver/transmitter (not shown) to facilitate that wireless communication. The communications network 1608 may use a FHSS integrated radio with digital input/outputs and signals, with the receiver/transmitters in the controller base station 1604 and flow enclosure base station 1606 being on the same high frequency that is unique to the overall air sampling/monitoring system 1600.

As shown, four separate air sampling devices 216a, 216b, 216c, and 216d are associated with the digital flow enclosure 1602. The digital flow enclosure 1602 is connected to the controller 202 by vacuum air lines 1610, and the air sampling devices 216a, 216b, 216c, and 216d are connected to the digital flow enclosure 1602 by atrium air flow lines 1612. The controller 202 is configured so that each vacuum air line 1610 and atrium air flow line 1612 carries 1 CFM of air, which is the desired air flow rate needed to conduct a proper sampling cycle at the air sampling devices 216a, 216b, 216c, and 216d. By way of comparison, like the inline flow control modules 904a, 904b, 904c, and 904d in the embodiment illustrated in FIG. 9, the digital flow enclosure 1602 illustrated in FIG. 16 is positioned between the air sampling devices 216a, 216b, 216c, and 216d and the controller 202. The digital flow enclosure 1602 can be calibrated for each individual air sampling device 216a, 216b, 216c, . . . , and 216h and is accurate to a flow rate of ±5 percent of 1 CFM.

The controller 202 is in electrical communication with the controller base station 1604 via a first group of signal wires 1614 and the digital flow enclosure 1602 is in electrical communication with the flow enclosure base station 1606 via a second group of signal wires 1616. The touchpanel 214 is in electrical communication with the controller 202 via signal wires 218. The first and second group of signal wires 1614 and 1616 are routed to and from the digital flow enclosure 1602 to provide a single, central location for measuring, monitoring, and controlling the flow rates at the various air sampling devices 216a, 216b, 216c, or 216d. As shown, the vacuum air line 1610 and first group of signal wires 1614 are connected at a respective port 308a, 308b, 308c, and 308d of the controller 202. The ports 308a, 308b, 308c, and 308d, which are illustrated more clearly in FIG. 3, are each dedicated to a respective air sampling device 216a, 216b, 216c, or 216d and not shared with any other ports.

Although the controller 202 and the controller base station 1604, the controller 202 and the touchpanel 214, and the digital flow enclosure 1602 and the flow enclosure base station 1606 are shown in wired communication with one another, it should be appreciated that those components of the sampling/monitoring system 1600 can also be in wireless communication via receiver/transmitters in each of those components. And, although the controller base station 1604 and the flow enclosure base station 1606 are shown in wireless communication with each other over network 1608, it should also be appreciated that those components of the sampling/monitoring system 1600 can also be in wired communication. In addition, because those components communicate with each other in series, any intermediary component can be removed from the sampling/monitoring system 1600 if desired. For example, the controller 202 can be wired directly to or in direct wireless communication with the digital flow enclosure 1602, thereby eliminating the need for the controller base station 1604 and the flow enclosure base station 1606. Or, the controller 202 and the digital flow enclosure 1602 can be wired directly to or in direct wireless communication with the controller base station 1604, thereby eliminating the need for the flow enclosure base station 1606.

The touchpanel 214 is connected in a parallel manner to the ports 308a, 308b, 308c, and 308d of the controller 202, which is connected in a parallel manner to the controller base station 1604. And, the flow enclosure base station 1606 is connected in a parallel manner to the digital flow enclosure 1602. It should be apparent, however, that the touchpanel 214, the controller 202, the controller base station 1604, the flow enclosure base station 1606, and the digital flow enclosure 1602 can be connected in any suitable manner. For example, the ports 308a, 308b, 308c, and 308d of the controller 202 can have identification codes, and the touchpanel 214 can communicate with the different ports 308a, 308b, 308c, and 308d by use of those ID codes via a common connection (e.g., a single signal wire). And, because each of the components is connected in series, certain intermediate components may be removed or incorporated into other components. For example, the ports 308a, 308b, 308c, and 308d of the controller 202 can be directly connected to the digital flow enclosure 1602 so that neither the controller base station 1604 nor the flow enclosure base station 1606 need to be utilized.

The controller 202 has an AC power supply 406 (FIG. 4) that supplies power to various components of the sampling/monitoring system 900, such as the touchpanel 214. The inner flow base station 1604 and outer flow base station 1606 may also have their own AC power supply (not shown). The digital flow enclosure 1602 receives its power from its electrical connection with the outer flow base station 1606 via the second group of signal wires 1616. It will be appreciated, however, that each of the components of the sampling/monitoring system 1600 can have its own power source or can be powered via an electrical connection with the controller 202, as conditions permit or require.

Figure 17:
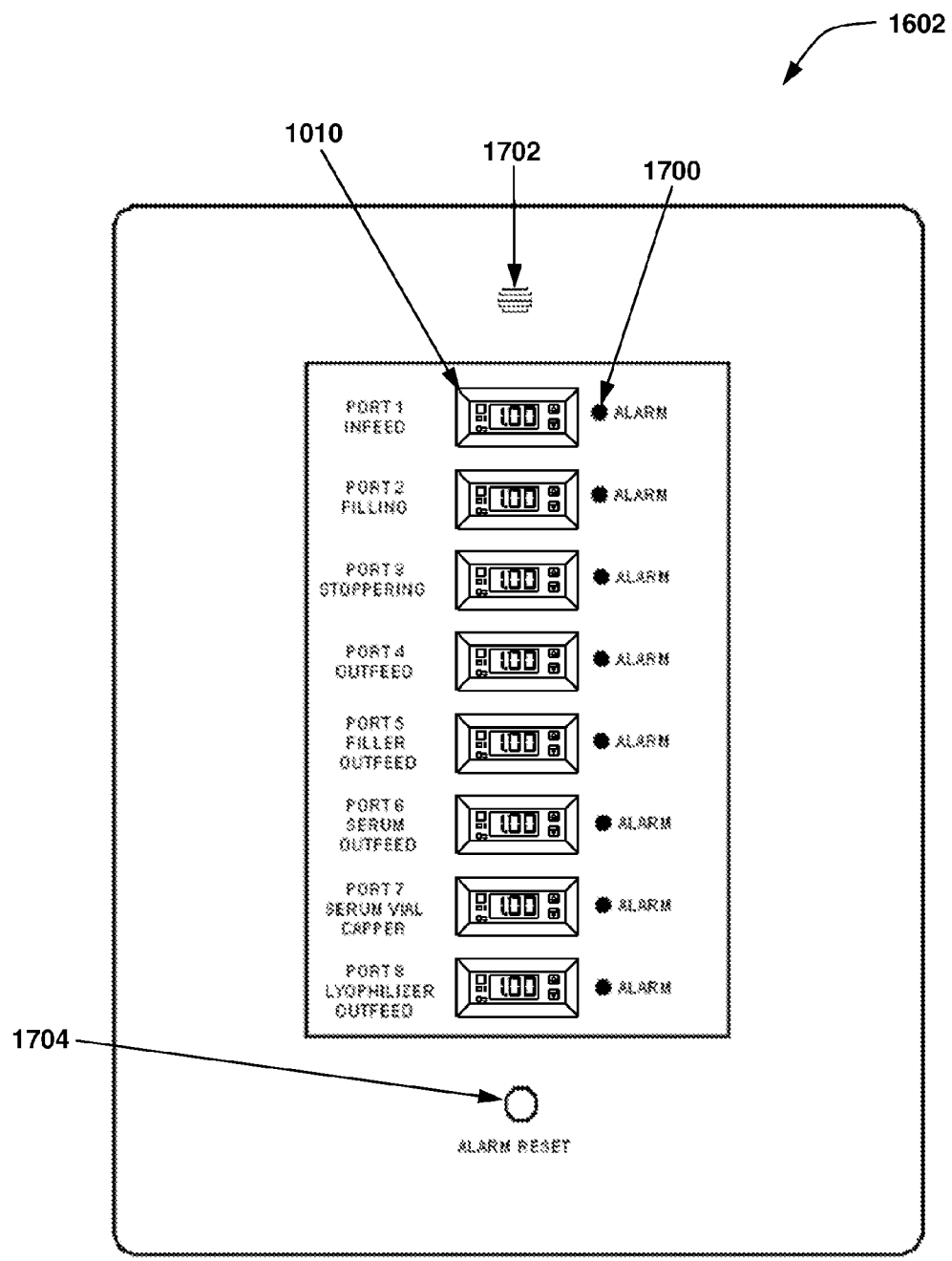
FIG. 17 is a detailed front view of the digital flow enclosure according to a non-limiting embodiment of the present invention.

Turning to FIG. 17, the front of a digital flow enclosure 1602 is shown in greater detail. The digital flow enclosure illustrated in FIG. 17 is configured to connect to eight air sampling devices 216a, 216b, 216c, . . . , and 216h. The digital flow enclosure 1602 includes a display interface 1010 for measuring, monitoring, and controlling the flow rate at each of the eight air sampling devices 216a, 216b, 216c, . . . , and 216h. The features and functionality of the display interface 1010 are similar to those described above in connection with FIG. 13B. For example, the display interface 1010 has a digital LED display 1300 that, unlike conventional rotameters, can be read from multiple angles and distances, has various buttons 1302-1308 that allow the user to set the desired range of flow rates, and has a digital flow switch 1200 that detects the flow rate coming in from the atrium air flow line 1612 and passing through to the vacuum air line 1610. Using a separate digital flow switch 1200 for each air sampling device 216a, 216b, 216c, and 216d, the digital flow enclosure 1602 measures and displays the actual flow rate that is realized at each respective air sampling device 216a, 216b, 216c, and 216d. Accordingly, providing a display interface 1010 for each of a number n of corresponding air sampling devices 216a, 216b, 216c, . . . , and 216n provides advantages over the inline flow control modules 904a, 904b, 904c, and 904d of the embodiment illustrated in FIG. 9 by providing the digital flow enclosure 1602 as a single, central location where the flow rates at various air sampling devices 216a, 216b, 216c, . . . , and 216n located throughout a clean room 102 can be measured, monitored, and controlled. The digital flow enclosure 1602 generates a flow alert/alarm when the flow measured for an air sampling device 216a, 216b, 216c, or 216d is outside of a desired flow rate.

The digital flow enclosure 1602 includes a visual alert indicator 1700, such as an LED, for each display interface 1010 and, therefore, for each air sampling device 216a, 216b, 216c, . . . , and 216h. The visual alert indicators 1700 indicate if the air flow for a specific air sampling device 216a, 216b, 216c, . . . , or 216h, as measured at the digital flow enclosure 1602, is outside of the desired flow rate. The detection performed by the digital flow switch 1200 at the digital flow enclosure 1602 is independent of the flow rate detection performed by the air flow switch 404 at the controller 202 so that the flow rate is simultaneously monitored at two locations for each air sampling device 216a, 216b, 216c, . . . , and 216h during a sampling cycle, thereby adding an additional measure of safety through redundancy.

The digital flow switch 1200 generates an alarm signal if the air flow rate measured at the controller 202 or the digital flow enclosure 1602 is not within the parameters set by the user (e.g., not within the range of 0.95-1.05 CFM). However, the sampling cycle continues until the user decides to abort the sampling cycle. Preferably, the digital flow enclosure 1602 provides an 8 second delay before the alarm signal is generated. That delay accounts for fluctuations that may occur during initial start-up of the system 1600 A typical sampling cycle may last between 10 minutes and 3 hours.

When an alarm signal is generated, a visual alert indicator 1700 is activated next to the display interface 1010 that corresponds to the air sampling device 216a, 216b, 216c, . . . , or 216h for which the flow rate is not within the parameters set by the user. An audible alarm 1702 is also activated at the digital flow enclosure 1602 in response to the alarm signal. The audible alarm 1702 will continue until the error conditions are removed and the flow rate returns to the desired level (e.g., 1 CFM). However, unlike described above for the inline flow control modules 904a, 904b, 904c, and 904d of the embodiment illustrated in FIG. 9, the visual alert indicator 1700 will remain on even after the error conditions are removed and the flow rate returns to the desired level. That feature allows a user to determine, some time after the alarm signal was generated and/or after the sampling cycle, which of the multiple air sampling devices 216a, 216b, 216c, . . . , and 216h connected to the digital flow enclosure 1602 experienced an error condition during the sampling cycle. Accordingly, the user to can remain focused on his or her work in the clean room 102 rather than having to immediately check which air sampling device 216a, 216b, 216c, . . . , or 216h is experiencing errors every time an audible error alert sounds.

The digital display enclosure 1602 also includes an alarm reset switch 1704. The alarm reset switch 1704 allows a user to manually reset (i.e., turn off) all of the visual alert indicators 1700 after identifying the air sampling device(s) 216a, 216b, 216c, . . . , and/or 216h at which errors occurred during a sampling cycle. If all of the error conditions have been removed and all of the flow rates have returned to the desired level, all of the visual alert indicators 1700 will turn off. For any air sampling device 216a, 216b, 216c, . . . , or 216h for which an error condition still exists, the visual alert indicator 1700 will remain on.

In the embodiment illustrated in FIG. 16, the touchpanel 214 will also receive the alarm signal when the air flow rate measured at the controller 202 or the digital flow enclosure 1602 is not within the parameters set by the user. Accordingly, the visual alert indicator 700 and the audible alarm 702 on the touchpanel 214 will also be activated if the air flow rate measured at the controller 202 or the digital flow enclosure 1602 is not within the parameters set by the user. Initiating the alarm reset switch 1704 at the digital flow enclosure 1602 will also reset the corresponding visual alert indicators 700 at the touchpanel 214.

The touchpanel 214 also includes an alarm reset switch 710 that will perform a similar function, resetting the visual alert indicators 700 and 1700 at both the touchpanel 214 and digital flow enclosure 1602, respectively. The alarm reset switch 710 at the touchpanel 214, however, will only reset the individual visual alert indicator 700 and 1700 that corresponds to the individual display 704a, 704b, 704c, or 704d and, therefore, the individual air sampling device 216a, 216b, 216c, or 216h corresponding to that display 704a, 704b, 704c, or 704d. Accordingly, the alarm reset switch 1704 allows all of the individual visual alert indicators 700 and 1700 for all of the air sampling devices 216a, 216b, 216c, and 216d to be reset from a single, central location rather than requiring the user to manually reset each individual visual alert indicator 700 and 1700, as is required at the touchpanel 214. Although not shown in the embodiments illustrated in FIGS. 7 and 16, the touchpanel 214 may also be provided with an alarm reset switch that provides a global system reset like the alarm reset switch 1704 provided on the digital flow enclosure. Resetting all of the visual alert indicators 700 and 1700 at the same time will not affect the individual function of the ports 308a, 308b, 308c, and 308d of the controller 202.

Also in the embodiment illustrated in FIG. 16, the touchpanel 214 provides the functionality for starting and stopping sampling cycles. As discussed above, the touchpanel 214 includes a start switch 706 for powering up the individual ports 308a, 308b, 308c, and 308d of the controller 202 to start a sampling cycle and an stop switch 708 for sending an abort signal to the controller 202 that stops a sampling cycle already in progress. Air flow is only activated and de-activated when the user manually operates the start switch 706 and stop switch 708, respectively. And, each start switch 706 and stop switch 708 only activates and de-activates the air flow for the particular air sampling device 216a, 216b, 216c, or 216d that corresponds to the display 704a, 704b, 704c, or 704d at which that the start switch 706 or stop switch 708 is located on the touchpanel 214. The touchpanel 214 can be used to activate the various ports 308a, 308b, 308c, and 308d of the controller 202, which will activate the respective display interfaces 1010 and digital flow switches 1200 at the digital flow enclosure 1602.

The touchpanel 214 and digital flow enclosure 1602 are preferably located near and/or adjacent to each other in a clean room 102. That way, the touchpanel 214 can be used in conjunction with the digital flow enclosure 1602 to verify that the air sampling devices 216a, 216b, 216c, or 216d associated with the touchpanel 214 and digital flow enclosure 1602 are all properly set up and ready to perform a sampling cycle. In that configuration, a user can start and stop air flow to any combination air sampling devices 216a, 216b, 216c, and/or 216d in the sampling/monitoring system 1600 from a single, central location. The user can also measure, monitor, and control the flow rates to each of those air sampling devices 216a, 216b, 216c, and 216d from that same location. By comparison, the inline flow control modules 904a, 904b, 904c, and 904d of the embodiment illustrated in FIG. 9 only allow the user to measure, monitor, and control the flow rate to the air sampling device 216a, 216b, 216c, or 216d that corresponds to the inline flow control module 904a, 904b, 904c, and 904d at which the user is located.

Figure 18:
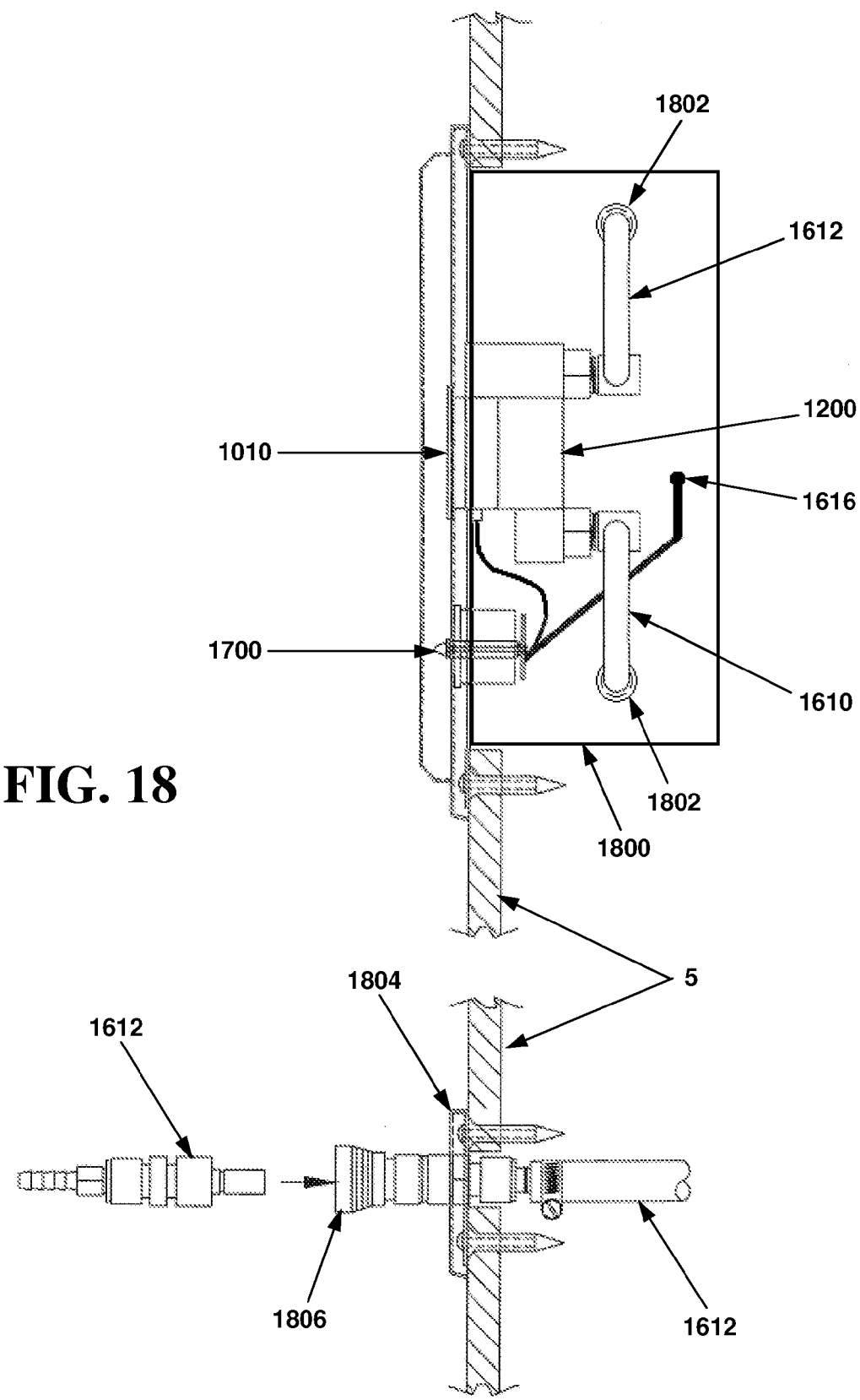
FIG. 18 is a detailed top view, taken in section, of the digital flow enclosure shown in FIG. 17 according to a non-limiting embodiment of the present invention.

The digital flow enclosure 1602 may be configured as a wall-mountable or benchtop unit. Referring to FIG. 18, a wall-mountable configuration of the digital flow enclosure 1602 is shown, including its digital flow switch 1200. The digital flow enclosure 1602 can be contained within a housing 1800 and mounted either internal to a wall 5, as shown, or externally to the face of the wall 5. The electronics of the digital flow enclosure 1602 may be sealed inside the housing 1800 so that the device may be disinfected like other portions of the clean room 102. As further illustrated in FIG. 18, air flow line adapters 1802 are provided at the bottom end of the digital flow enclosure 1602 and extend through the housing to so the vacuum air line 1610 and the atrium air flow line 1612 maintain fluid communication through the housing 1800.

One end of the digital flow switch 1200 is connected to the vacuum air line 1610 and the opposite end is connected to the atrium air flow line 1612. To allow the air sampling devices 216a, 216b, 216c, and 216d to be placed at locations in the clean room 102 that are not near the digital flow enclosure 1602, quick disconnect outlets 1804 can be placed in the wall 5 at locations in the clean room 102 away from the digital flow enclosure 1602 and nearer to the respective the air sampling devices 216a, 216b, 216c, and 216d. Each atrium air flow line 1612 connected to the digital flow enclosure 1602 can then be routed to a corresponding quick disconnect outlet 1804 where the atrium air flow line 1612 connected to each air sampling device 216a, 216b, 216c, and 216d can be placed in fluid communication with the digital flow enclosure 1602 via a plug adapter 1806. The plug adapter 1806 is preferably a quick disconnect so that the atrium air flow line 1612 can be quickly connected and disconnected and replaced, if necessary. That feature reduces the length of the atrium air flow line 1612 between the wall 5 and each air sampling device 216a, 216b, 216c, and 216d in the clean room 102, which helps prevent tangling, kinking, breakage, etc. of the atrium air flow lines 1612. The remainder of the atrium air flow lines 1612 remain behind the wall 5.

The flow enclosure base station 1606 is preferably located outside of the clean room 102 in an adjacent room 104. The second group of signal wires 1616 also connect to the rear face of the digital flow enclosure 1602 and can also run behind and/or through the wall to connect the digital flow enclosure 1602 to the flow enclosure base station 1606. The flow enclosure base station 1606 isolates the digital flow enclosure 1602 from the controller 202. Thus, the DC voltage and logic signals connected to the digital flow enclosure 1602 are isolated from the controller 202. That is done so that a short in the controller 202 does not cause a short in the digital flow enclosure 1602 and the digital flow enclosure 1602 can then be controlled by another device, such as the touchpanel 214. The controller base station 1604 functions in a similar manner. Accordingly, the controller base station 1604 and flow enclosure base station 1606 are effectively repeaters that pass signals between the digital flow enclosure 1602 and the controller 202 and that electrically isolate the controller 202.

It should be apparent that the controllers 202 and 804, the touchpanel 214, the touchpanel base station 302, the inline flow control modules 904, the inline flow control base station 950, the digital flow enclosure 1602, the controller base station 1604, and the flow enclosure base station 1606 can each be implemented by a processor or other computing platform, such as the computing device 210, to control the operation of those devices. In addition, although each of those components is shown and described as being a separate device, they can be integrated in any combination into a single unit. In addition, each of those components can have a separate processor, or they can all share a single processor.

Each of the sampling/monitoring systems 200, 800, 900, and 1600 can be in a network configuration or a variety of data communication network environments using software, hardware or a combination of hardware and software to provide the processing functions. All or parts of the systems 200, 800, 900, and 1600 and their associated processes can be stored on or read from computer-readable media, such as a CD-ROM or instructions received online and carried over a transmission line or contained in a customized hardwired application specific integrated circuit (ASIC).

Although certain presently preferred embodiments of the disclosed invention have been specifically described herein, it will be apparent to those skilled in the art to which the invention pertains that variations and modifications of the various embodiments shown and described herein may be made without departing from the spirit and scope of the invention. Accordingly, it is intended that the invention be limited only to the extent required by the appended claims and the applicable rules of law.

What is claimed is:

1. A system for sampling air at multiple locations in a controlled environment comprising:
    two or more air sampling devices at different locations within the controlled environment;
    a controller at a location outside of the controlled environment and in separate air flow communication with each of the two or more air sampling devices via separate first vacuum tubes, the controller having a manifold configured to separately control a rate of air flow from the two or more air sampling devices to the controller via each of the separate first vacuum tubes and to selectively direct the air flow from each of the separate first vacuum tubes to one or more second vacuum tubes;
    a vacuum source at a location outside the controlled environment and in air flow communication with the controller via the one or more second vacuum tubes, the vacuum source providing suction and being controlled by the controller to generate the air flow through each of the first vacuum tubes; and
    a flow switch for each of the two or more air sampling devices at a location between a corresponding air sampling device and the vacuum source, each of the flow switches being configured to separately measure and control the rate of air flow through a corresponding first vacuum tube,
    wherein an alarm is automatically activated at a location inside the controlled environment by one or more of the flow switches when the rate of air flow measured at one or more of the flow switches deviates from a desired value by a predetermined amount.

2. The system of claim 1, wherein
    each flow switch is provided at a location inside the controlled environment and between its corresponding air sampling device and the controller.

3. The system of claim 2, wherein
    an alarm at the controller and/or one or more of the flow switches is automatically activated when the rate of air flow measured at one or more of the flow switches deviates from the desired value by the predetermined amount.

4. The system of claim 2, further comprising
    a second flow switch provided at the controller for each of the two or more air sampling devices, each of the second flow switches being configured to separately measure and control the rate of air flow through a corresponding first vacuum tube.

5. The system of claim 4, wherein
    an alarm at one or more of the controller, the one or more flow switches, and the one or more second flow switches is automatically activated when the rate of air flow measured at the one or more flow switches and/or the one or more second flow switches deviates from the desired value by the predetermined amount.

6. The system of claim 1, further comprising a second controller at a location outside of the controlled environment and in separate air flow communication with each of one or more second air sampling devices via separate third vacuum tubes.

7. The system of claim 6, wherein
    an alarm at one or more of the controller, the second controller, and the location inside the controlled environment is automatically activated when the rate of air flow measured at one or more of the flow switches deviates from the desired value by the predetermined amount.

8. The system of claim 1, wherein the vacuum source is activated by communicating a control signal from at least one flow switch to the controller and from the controller to the vacuum source.

9. The system of claim 1, further comprising
a purge vacuum source in air flow communication with the two or more air sampling devices, wherein
the two or more air sampling devices are isolated from the controlled environment,
a signal is communicated from the controller to the purge vacuum source to draw a predetermined volume of a fluid through the two or more air sampling devices, the fluid being at least one of a gas and a vapor, and
a signal is output by the controller when the predetermine volume of the fluid has been collected.

10. The system of claim 1, further comprising
a digital flow enclosure at a location inside the controlled environment,
wherein the digital flow enclosure houses each of the flow switches corresponding to each of the two or more air sampling devices.

11. A method for sampling air at multiple locations in a controlled environment, comprising the steps of:
providing two or more air sampling devices at different locations within the controlled environment;
providing a controller at a location outside of the controlled environment and in separate air flow communication with each of the two or more air sampling devices via separate first vacuum tubes, the controller having a manifold configured to separately control a rate of air flow from the two or more air sampling devices to the controller via each of the separate first vacuum tubes and to selectively direct the air flow from each of the separate first vacuum tubes to one or more second vacuum tubes;
providing a vacuum source at a location outside the controlled environment and in air flow communication with the controller via the one or more second vacuum tubes, the vacuum source providing suction and being controlled by the controller to generate the air flow through each of the first vacuum tubes;
providing a flow switch for each of the two or more air sampling devices at a location between a corresponding air sampling device and the vacuum source, each of the flow switches being configured to separately measure and control the rate of air flow through a corresponding first vacuum tube; and
automatically activating an alarm at a location inside the controlled environment when the rate of air flow measured at one or more of the flow switches deviates from a desired value by a predetermined amount.

12. The method of claim 11, further comprising the step of providing each flow switch at a location inside the controlled environment and between its corresponding air sampling device and the controller.

13. The method of claim 12, further comprising the step of automatically activating an alarm at the controller and/or one or more of the flow switches when the rate of air flow measured at the one or more flow switches deviates from the desired value by the predetermined amount.

14. The method of claim 12, further comprising the step of providing a second flow switch at the controller for each of the two or more air sampling devices, each of the second flow switches being configured to separately measure and control the rate of air flow through a corresponding first vacuum tube.

15. The method of claim 14, further comprising the step of automatically activating an alarm at one or more of the controller, the one or more flow switches, and the one or more second flow switches when the rate of air flow measured at the one or more flow switches and/or the one or more second flow switches deviates from the desired value by the predetermined amount.

16. The method of claim 11, further comprising the step of providing a second controller at a location outside of the controlled environment and in separate air flow communication with each of one or more second air sampling devices via separate third vacuum tubes.

17. The method of claim 16, further comprising the step of automatically activating an alarm at one or more of the controller, the second controller, and the location inside the controlled environment when the rate of air flow measured at one or more of the flow switches deviates from the desired value by the predetermined amount.

18. The method of claim 11, further comprising the step of activating the vacuum source by communicating a control signal from at least one flow switch to the controller and from the controller to the vacuum source.

19. The method of claim 11, further comprising the steps of:
providing a purge vacuum source in air flow communication with the two or more air sampling devices;
isolating the two or more air sampling devices from the controlled environment;
communicating a signal from the controller to the purge vacuum source to draw a predetermined volume of a fluid through the two or more air sampling devices, the fluid being at least one of a gas and a vapor; and
outputting a signal when the predetermine volume of the fluid has been collected.

20. The method of claim 11, further comprising the step of providing digital flow enclosure at a location inside the controlled environment, the digital flow enclosure housing the flow switches corresponding to each of the two or more air sampling devices.

* * * * *